US010258741B2

United States Patent
Gravesen et al.

(10) Patent No.: US 10,258,741 B2
(45) Date of Patent: Apr. 16, 2019

(54) MICROFLUIDIC FLOW RESTRICTOR AND SYSTEM

(71) Applicant: CeQur SA, Horw (CH)

(72) Inventors: Peter Gravesen, Nordborg (DK); Bo F. Madsen, Sydals (DK)

(73) Assignee: CeQur SA, Horw (CH)

( * ) Notice: Subject to any disclaimer, the term of this patent is extended or adjusted under 35 U.S.C. 154(b) by 0 days.

(21) Appl. No.: 15/392,671

(22) Filed: Dec. 28, 2016

(65) Prior Publication Data
US 2018/0177941 A1    Jun. 28, 2018

(51) Int. Cl.
| | |
|---|---|
| *A61M 5/14* | (2006.01) |
| *A61M 5/36* | (2006.01) |
| *A61M 5/168* | (2006.01) |
| *A61M 5/142* | (2006.01) |

(52) U.S. Cl.
CPC ........ *A61M 5/16804* (2013.01); *A61M 5/141* (2013.01); *A61M 5/14248* (2013.01); *A61M 5/16854* (2013.01); *A61M 5/16886* (2013.01); *A61M 5/36* (2013.01); *A61M 2205/3334* (2013.01); *A61M 2205/3337* (2013.01)

(58) Field of Classification Search
CPC .......... A61M 5/16804; A61M 5/16886; A61M 5/14248; A61M 5/16854; A61M 5/36
See application file for complete search history.

(56) References Cited

U.S. PATENT DOCUMENTS

| | | | |
|---|---|---|---|
| 3,898,637 A | * | 8/1975 | Wolstenholme .......... F17D 3/01 128/DIG. 13 |
| 4,037,596 A | | 7/1977 | LeFevre et al. |
| 4,192,303 A | | 3/1980 | Young et al. |

(Continued)

FOREIGN PATENT DOCUMENTS

| | | |
|---|---|---|
| CA | 2768779 A1 | 1/2011 |
| CN | 101907631 A | 12/2010 |

(Continued)

OTHER PUBLICATIONS

Barigou, et al. "A capillary suction probe for bubble size measurement", Measurement Science and Technology, IOP Publishing, Bristol, GB, vol. 2, No. 4, Apr. 1, 1991 (9 pages).

(Continued)

*Primary Examiner* — Edelmira Bosques
(74) *Attorney, Agent, or Firm* — Eversheds Sutherland (US) LLP

(57) ABSTRACT

Embodiments of the present invention relate to a microfluidic flow restrictor having a converging tapered inlet connected by a constant internal diameter section to a diverging tapered outlet having an outlet face and a smooth and gradual transition from the constant internal diameter section to the outlet face. This dual tapered capillary flow restrictor may be incorporated into a system such as a microfluidic circuit. Using a dual tapered capillary for accurate flow control together with a constant pressure source provides a more steady flow with reduced flow fluctuation caused by bubbles passing or pinning to the capillary end-face. Further, when connected in series, these dual tapered capillary flow restrictors may reduce noise in flow and pressure measurements, reduce bubble segmentation, and reduce bubble pinning.

8 Claims, 12 Drawing Sheets

(56) References Cited

U.S. PATENT DOCUMENTS

| | | |
|---|---|---|
| 4,312,010 A | 1/1982 | Doring |
| 4,699,615 A | 10/1987 | Fischell et al. |
| 4,756,884 A | 7/1988 | Hillman et al. |
| 4,931,120 A | 6/1990 | Christoff |
| 4,934,375 A | 6/1990 | Cole et al. |
| 5,085,058 A | 2/1992 | Aaron et al. |
| 5,489,265 A | 2/1996 | Montalvo et al. |
| 5,772,936 A | 6/1998 | Cavender |
| 6,012,902 A | 1/2000 | Parce |
| 6,027,479 A | 2/2000 | Alei et al. |
| 6,102,897 A | 8/2000 | Lang |
| 6,116,718 A | 9/2000 | Peeters et al. |
| 6,196,525 B1 | 3/2001 | Ganan-Calvo |
| 6,328,421 B1 | 12/2001 | Kojima et al. |
| 6,360,775 B1 | 3/2002 | Barth et al. |
| 7,311,882 B1 | 12/2007 | Renzi |
| 7,431,052 B2 | 10/2008 | Gravesen et al. |
| 8,563,325 B1 | 10/2013 | Bartsch et al. |
| 8,887,525 B2 | 11/2014 | Harman et al. |
| 8,940,147 B1 | 1/2015 | Bartsch et al. |
| 9,015,945 B2 | 4/2015 | Poulsen et al. |
| 2001/0037106 A1 | 11/2001 | Shadduck |
| 2001/0042712 A1 | 11/2001 | Battrell et al. |
| 2002/0022846 A1 | 2/2002 | Auge |
| 2002/0075363 A1 | 6/2002 | McNeely et al. |
| 2002/0097633 A1 | 7/2002 | O'Connor et al. |
| 2002/0132265 A1 | 9/2002 | Kopf-Sill |
| 2003/0039978 A1 | 2/2003 | Hannah |
| 2003/0196714 A1 | 10/2003 | Gilbert et al. |
| 2003/0211631 A1 | 11/2003 | Skinner et al. |
| 2004/0053268 A1 | 3/2004 | Karlsen |
| 2004/0166555 A1 | 8/2004 | Braff et al. |
| 2004/0172966 A1 | 9/2004 | Ozaki et al. |
| 2004/0202994 A1 | 10/2004 | Timperman |
| 2004/0219507 A1 | 11/2004 | Abed |
| 2005/0169778 A1 | 8/2005 | Blankenstein et al. |
| 2005/0173003 A1 | 8/2005 | Laverdiere et al. |
| 2006/0034735 A1 | 2/2006 | Miura et al. |
| 2006/0041248 A1* | 2/2006 | Patton ............. A61J 3/00 604/890.1 |
| 2006/0099116 A1 | 5/2006 | Manger et al. |
| 2006/0264779 A1 | 11/2006 | Kemp et al. |
| 2007/0006926 A1 | 1/2007 | Prakash et al. |
| 2007/0012371 A1 | 1/2007 | Gravesen et al. |
| 2007/0092172 A1 | 4/2007 | Obara et al. |
| 2007/0117212 A1 | 5/2007 | Kautz et al. |
| 2007/0199269 A1 | 8/2007 | Mees et al. |
| 2008/0171077 A1 | 7/2008 | Gray |
| 2008/0199816 A1 | 8/2008 | Choi et al. |
| 2010/0069830 A1 | 3/2010 | Grigorov |
| 2010/0112723 A1 | 5/2010 | Battrell et al. |
| 2010/0124759 A1 | 5/2010 | Wang et al. |
| 2010/0281990 A1* | 11/2010 | Gravesen ............. A61M 5/142 73/715 |
| 2010/0282766 A1 | 11/2010 | Arndt |
| 2011/0066108 A1 | 3/2011 | Geipel et al. |
| 2011/0081677 A1 | 4/2011 | Luo et al. |
| 2011/0287948 A1 | 11/2011 | Suresh et al. |
| 2012/0015428 A1 | 1/2012 | Seale et al. |
| 2012/0048391 A1 | 3/2012 | Delamarche et al. |
| 2012/0328488 A1 | 12/2012 | Puntambekar et al. |
| 2013/0004385 A1 | 1/2013 | Lee et al. |
| 2013/0055896 A1 | 3/2013 | Lavric et al. |
| 2013/0078164 A1 | 3/2013 | Baroud et al. |
| 2013/0112612 A1 | 5/2013 | Blankenstein et al. |
| 2013/0206250 A1 | 8/2013 | Zhang et al. |
| 2014/0166476 A1 | 6/2014 | Abraham et al. |
| 2014/0220606 A1 | 8/2014 | Puntambekar et al. |
| 2014/0299672 A1 | 10/2014 | Gopalan et al. |
| 2016/0209431 A1 | 7/2016 | Battrell et al. |

FOREIGN PATENT DOCUMENTS

| | | | |
|---|---|---|---|
| EP | 0737483 A1 | 10/1996 | |
| EP | 2295096 A1 | 3/2011 | |
| WO | WO-96/23534 A1 | 8/1996 | |
| WO | WO-05/023339 A1 | 3/2005 | |
| WO | WO 2008024224 A2 * | 2/2008 | ......... A61M 1/3655 |
| WO | WO-15/092611 A1 | 6/2015 | |
| WO | WO-16/006202 A1 | 1/2016 | |

OTHER PUBLICATIONS

Jensen, et al. "The clogging pressure of large bubbles in microchannel contractions", Mikroelektronick Centret (MIC), Technical University of Denmark, Jun. 7, 2003 (22 pages).

Jensen, et al., "Quasi-static motion of bubbles in microchannel contractions", Mikroelektronik Centret (MIC), Technical University of Denmark, updated (4 pages).

International Search Report for Application No. PCT/DK2004/000587, dated Nov. 19, 2004 (5 pages).

Written Opinion for Application No. PCT/DK2004/000587 dated Mar. 13, 2003 (8 pages).

International Search Report and Written Opinion for PCT/EP2017/084418, dated Apr. 11, 2018 (15 pages).

* cited by examiner

MICROFLUIDIC FLOW RESTRICTOR AND SYSTEM

FIELD OF THE INVENTION

In general, embodiments of the present invention relate to apparatus for delivering a controlled or restricted flow of liquid and, more specifically, to flow restricting elements adapted to manage bubbles formed within the liquid flow.

BACKGROUND

In medical infusion, the flow typically needs to be restricted to rather low rates, such as, for example, 1000 microliters per hour. Delivery of liquids at flow rates of up to a few milliliters per hour or less may be achieved by connecting a source of pressurized liquid to a capillary of small internal diameter. The rate of flow through the capillary has a well-defined relation to the length and internal diameter of the capillary, and to the difference in pressure between the capillary inlet and the capillary outlet. For any given pressure difference, the flow rate may be fixed at a desired value by choosing a capillary of suitable length and internal diameter.

A problem with capillaries of very small internal diameter (i.e., micro-capillaries) is that bubbles of gas in the liquid may have a serious impact on the pressure difference or pressure drop required to drive a given flow rate through the capillary and, in the worst case, bubbles may lead to an effective blocking of the capillary. This is due to the phenomenon of fragmentation of a larger bubble at the inlet of the capillary into a plurality of small bubbles within the capillary. The small bubbles are separated from each other by plugs of liquid and each small bubble requires a certain pressure difference between its ends to move along the capillary. That pressure difference is largely independent of bubble length. Bubble fragmentation at the inlet may fill the capillary with so many small bubbles that the pressure difference available for generating liquid flow is reduced or fully consumed by the sum of pressure drops needed to drive the small bubbles along the capillary. Therefore, flow through the capillary may be severely reduced or even stopped by bubble fragmentation.

Fused silica micro-capillaries with a constant internal diameter of 10 to 100 micrometers are widely used in the field of chemical analysis, in applications such as capillary electrophoresis and gas chromatography. Micro-capillary flow restrictors for use in medical infusion are made by cutting suitable lengths, for example a few centimeters each, off of fused silica micro-capillary stock. Other choices of material are also available, such as polymeric capillaries or micro-machined planar capillary structures.

Unfortunately, however, experience shows that the occurrence of bubble fragmentation in such known micro-capillary flow restrictors is not predictable. Out of 100 flow restrictors made, some 65 or so may have a very low tendency towards bubble fragmentation; whereas, others will fragment virtually any bubble that enters.

There is a lack of yield and a lack of predictability. Both are major obstacles in the industrial use of micro-capillary flow restrictors, for example in mass fabrication of medical infusion devices. See, for example, U.S. Pat. No. 7,431,052 for one approach to understanding and addressing the bubble fragmentation problem, the disclosure of which is incorporated herein by reference in its entirety. While achieving some success in addressing this issue through the use of a flow restrictor having an inlet with a particular contour that has less tendency towards bubble fragmentation, nonetheless bubble fragmentation still occurs. While the inlet contour is more predictable in its bubble fragmentation behavior and provides a higher yield of usable devices than conventional micro-capillary flow restrictors, problems still remain.

SUMMARY

The present disclosure relates to a flow restrictor that manages bubbles in an improved manner, particularly well-suited for use in microfluidic devices, such as patch pumps and other medical infusion devices, that include sensors that are sensitive to flow noise.

In various embodiments, this is achieved by a flow restrictor with a flow channel having over most of its length a substantially constant, minimum hydraulic diameter $D=4 A/W$, where A is the minimum local cross-sectional area of the channel and W is the minimum local wetting perimeter of the channel. The flow restrictor may have a converging inlet and a diverging outlet. For example:

at distances z from the inlet face when $0<z<z_1$, the channel has a hydraulic diameter $D_z \geq k*D$ wherein $k \geq 3.5$, in some cases $3.5 \geq k \geq 1.3$;

at distances z from the inlet face when $z_1<z<z_2$, the channel has a hydraulic diameter $D_z$ with $k*D \geq D_z \geq D$;

at distances z from the inlet face when $z_2<z<z_3$, the channel has a hydraulic diameter $D_z$ with $D_z \approx D$ (e.g., $D_z = D \pm 0.02$ D);

at distances z from the inlet face when $z_3<z<z_4$, the channel has a hydraulic diameter $D_z$ with $k*D \geq D_z \geq D$; and at distances z from the inlet face when $z_4<z$, the channel has a hydraulic diameter $D_z \geq k*D$.

It has been discovered that widening the flow channel at both the inlet and the outlet, such that the inner diameter converges/diverges smoothly and gradually, and preferably by a factor of at least 1.3 over a length of at least 3 channel diameters, significantly reduces the tendency towards bubble fragmentation in micro-capillary flow restrictors and, importantly, also substantially reduces the noise measured by flow or pressure sensors proximate or downstream of at least one flow restrictor.

In general, in a first aspect, an embodiment of the invention includes a microfluidic flow restrictor including a tube having a constant internal diameter section, a converging tapered inlet including an inlet face and a smooth and gradual transition from the inlet face to the constant internal diameter section, and a diverging tapered outlet including an outlet face and a smooth and gradual transition from the constant internal diameter section to the outlet face.

In various embodiments, the microfluidic flow restrictor may be a capillary. The microfluidic flow restrictor may include one or both of the inlet face and the outlet face having an internal diameter of at least two times an internal diameter of the constant diameter section. The constant internal diameter section may (i) begin at a distance of at least 20 times the internal diameter of the constant internal diameter section downstream of the inlet face and (ii) end at a distance of at least 10 times the internal diameter of the constant internal diameter section upstream of the outlet face. The internal diameter of the constant internal diameter section may be in a range up to about 100 μm, optionally in a range from about 5 μm to about 40 μm. In additional alternative embodiments, the internal diameter of the constant internal diameter section may be in a range up to about 40 μm, 60 μm, or 80 μm. A ratio of a length of the microfluidic flow restrictor divided by the internal diameter of the constant internal diameter section (i.e., L/D) may be less than 20,000. In alternative embodiments, the ratio may be less than 500, 1,000, or 10,000. In some embodiments, the ratio may be at least 100, or at least 50, or at least 30, or at least 10. The converging tapered inlet and the diverging tapered outlet may each be individually symmetric about a central longitudinal axis of the microfluidic flow restrictor. The converging tapered inlet and the diverging tapered outlet may also be symmetric with each other.

In various embodiments, the microfluidic flow restrictor may be adapted to transport a liquid having a flow rate in a range from about 1 µl/h to about 500 µl/h. The converging tapered inlet of the flow restrictor may be adapted to prevent or to reduce the likelihood of gas bubbles from segmenting into plugs of gas separated by plugs of liquid inside the constant internal diameter section, that are shorter than 10 times the inner diameter. The diverging tapered outlet may be adapted to (i) prevent or reduce the likelihood of a gas bubble from pinning to any structure inside the tapered outlet and/or (ii) allow a gas bubble to only pin to an irregular structure on the outlet face, if at all.

In general, in another aspect, an embodiment includes a microfluidic system including a wall defining a flow path for transporting a liquid, a sensor adapted to obtain a measurement of a flow characteristic of the liquid through the flow path, and a flow restrictor disposed in the flow path, the flow restrictor featuring (i) a converging tapered inlet including an inlet face and (ii) a diverging tapered outlet including an outlet face and the flow restriction being adapted to reduce a noise component of the measurement by the sensor.

In various embodiments, the diverging tapered outlet may be adapted to one or both of (i) prevent or reduce the likelihood of a gas bubble from pinning to only any structure inside the tapered outlet and (ii) allow a gas bubble to pin to an irregular structure on the outlet face, if at all. The liquid in the microfluidic system may include a medicament and the microfluidic system can be disposed within a patch pump adapted to deliver the medicament to a patient. The flow path in the microfluidic system may include a basal flow path adapted to deliver a basal dose to a patient. The microfluidic system may further include a bolus flow path arranged in parallel with the basal flow path. The sensor may include a flow rate sensor and/or a pressure sensor. The flow characteristic may include a flow rate and/or a pressure. The flow restrictor may include a first flow restrictor disposed upstream of the sensor and a second flow restrictor disposed downstream of the sensor. The converging tapered inlet may be adapted to segment a gas bubble entrained in the liquid. The flow restrictor may further include a constant internal diameter section between the converging tapered inlet and the diverging tapered outlet.

In various embodiments, the inlet face and/or the outlet face features an internal diameter of at least two times an internal diameter of the constant internal diameter section. The constant internal diameter section may (i) begin at a distance of at least 20 times the internal diameter of the constant internal diameter section downstream of the inlet face and (ii) end at a distance of at least 10 times the internal diameter of the constant internal diameter section upstream of the outlet face. The internal diameter of the constant internal diameter section may be in a range up to about 100 µm, optionally in a range from about 5 µm to about 40 µm. In additional alternative embodiments, the internal diameter of the constant internal diameter section may be in a range up to about 40 µm, 60 µm, or 80 µm. A ratio of a length of the microfluidic flow restrictor divided by the internal diameter of the constant internal diameter section (i.e., L/D) may be less than 20,000. In alternative embodiments, the ratio may be less than 500, 1,000, or 10,000. In some embodiments, the ratio may be at least 100, or at least 50, or at least 30, or at least 10. The flow restrictor may be adapted to reduce the noise component by at least 50 percent. In some embodiments, the flow restrictor reduces the noise component by at least 75 percent, e.g., to 85 percent or more.

In general, in another aspect, an embodiment includes a method of restricting a flow of a liquid. The method can include passing the liquid through a flow restrictor having (i) a converging tapered inlet including an inlet face and a smooth and gradual transition from the inlet face to a constant internal diameter section and (ii) a diverging tapered outlet including an outlet face and a smooth and gradual transition from the constant internal diameter section to the outlet face.

In various embodiments, the inlet face and/or the outlet face can feature an internal diameter of at least two times an internal diameter of the constant internal diameter section. The constant internal diameter section may (i) begin at a distance of at least 20 times the internal diameter of the constant internal diameter section downstream of the inlet face and (ii) end at a distance of at least 10 times the internal diameter of the constant internal diameter section upstream of the outlet face. The internal diameter of the constant internal diameter section may be in a range up to about 100 µm, optionally in a range from about 5 µm to about 40 µm. In additional alternative embodiments, the internal diameter of the constant internal diameter section may be in a range up to about 40 µm, 60 µm, or 80 µm. A ratio of a length of the microfluidic flow restrictor divided by the internal diameter of the constant internal diameter section (i.e., L/D) may be less than 20,000. In alternative embodiments, the ratio may be less than 500, 1,000, or 10,000. In some embodiments, the ratio may be at least 100, or at least 50, or at least 30, or at least 10. In some instances, the method may further include segmenting a gas bubble entrained in the liquid using the converging tapered inlet. The method may further include preventing or reducing the likelihood of a gas bubble from pinning to the outlet face.

In general, in another aspect, an embodiment includes a method of measuring a flow characteristic of a liquid in a flow path. The method can include the steps of (i) passing the liquid through a flow restrictor in the flow path, the flow restrictor including a converging tapered inlet having an inlet face and a diverging tapered outlet having an outlet face and (ii) obtaining a measurement of the flow characteristic of the liquid downstream of the flow restrictor using a sensor, where the diverging tapered outlet is adapted to reduce a noise component of the measurement.

In various embodiments, the flow characteristic may include one or both of a flow rate and a pressure. The sensor may include one or both of a flow rate sensor and a pressure sensor. The flow restrictor may be adapted to reduce the noise component by at least 50 percent. In some instances, the method may further include segmenting a gas bubble entrained in the liquid using the converging tapered inlet. In some cases, the method may further include preventing or reducing the likelihood of a gas bubble from pinning to the outlet face.

BRIEF DESCRIPTION OF THE DRAWINGS

In the drawings, like reference characters generally refer to the same parts throughout different views. Also, the drawings are not necessarily to scale, emphasis instead generally being placed upon illustrating the principles of the invention. In the following description, various embodiments of the invention are described with reference to the following drawings, in which.

DETAILED DESCRIPTION

Figure 1:
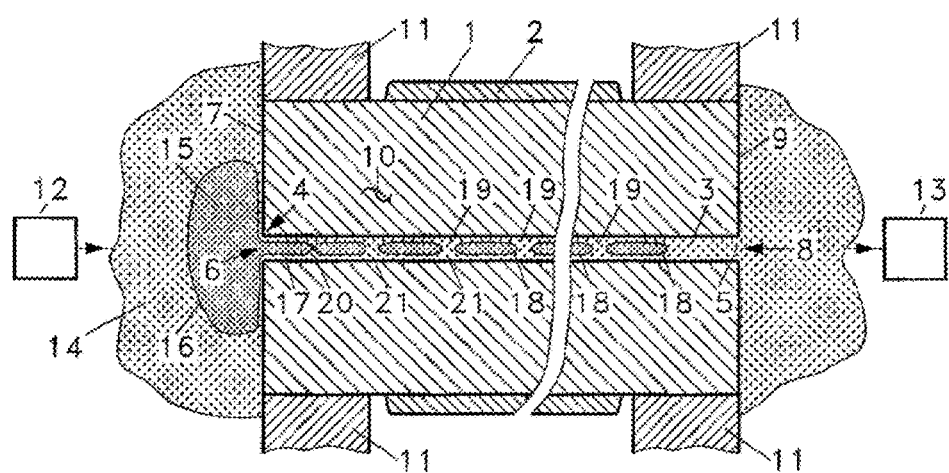
FIG. 1 is a schematic, side cross-section view of a prior art flow restrictor made by cutting a length off of micro-capillary stock.

FIG. 1 shows a conventional capillary flow restrictor 10 made by cutting off a length of micro-capillary which is commercially available from various vendors for use in the field of chemical analysis (e.g., gas chromatography, capillary electrophoresis, etc.).

The device 10 is an elongated tube whose wall 1 is made from fused silica (quartz glass) with an outer cladding 2 of polyimide. The wall 1 surrounds a flow channel 3 of circular or rectangular (for example, square) cross-section that extends from an inlet 4 to an outlet 5. At the inlet 4, the flow channel 3 forms an inlet opening 6 in an inlet face 7 of the flow restrictor, and at the outlet 5, the flow channel 3 forms an outlet opening 8 in an outlet face 9 of the flow restrictor 10. Depending on how the device was cut off, the inlet face 7 and the outlet face 9 of the device may be smooth (e.g., from abrasive cutting) as shown at 7 or slightly rough (e.g., from scoring and breaking) as shown at 9.

The flow restrictor 10 is often mounted in a flow system for delivering a controlled flow of liquid from a source 12 of liquid 14 to a recipient 13. The source 12 is pressurized in a suitable way, not shown, to a pressure that is higher than the pressure prevailing at the recipient 13. For example, in a medical infusion system, the source 12 may be an inflated bladder at a pressure of about 300-2000 mbar above recipient pressure, and the recipient 13 may be a blood vessel or any other suitable internal location in the body of a patient who has received the entire flow system as an implant.

Mounting detail is schematically indicated at both ends of the flow restrictor, where the polyimide cladding has been removed to allow direct contact between a fluid-tight clamping system, indicated as 11, of the flow system and the body 1 of the capillary tube. In other embodiments, the polyimide surface is bonded directly to the flow system by, e.g., adhesive applied to the polyimide surface.

When the conventional flow restrictor 10 is in use, the liquid 14 may contain bubbles of gas 15. One such bubble 16 is shown as being driven into the inlet 4 of the flow channel 3 by the pressure difference between source 12 and recipient 13. Often the presence of the bubble causes two-phase flow at the channel inlet 4. Liquid flows in a thin layer 17 that adheres to the inner surface of the channel 3. The liquid layer 17 coaxially surrounds a flow 18 of gas that fills the remaining core of the channel 3.

The two-phase flow in the flow channel 3 exhibits a phenomenon of instability, which frequently leads to fragmentation of the gas flow into separate bubbles 18 of gas separated by plugs 19 of liquid. This is due to the surface tension of the liquid-gas interface of the film 17. The surface tension causes a tendency of the liquid film to reduce its surface. Perturbations having a wavelength longer than βD (where D is the hydraulic diameter of the flow channel 3 and β is theoretically expected to be greater than 1, typically in a range of 1 to 2) may grow until a bubble is pinched off 20, 21. Such fragmentation is frequently observed, although its onset has turned out in practice to be largely unpredictable. The fragmentation can lead to the generation of a plurality of small bubbles each having a length $L_{min}$ of the order of the wetted perimeter of the channel, βD. β is the aspect ratio of the bubble, a dimensionless constant, that is equal to a ratio between inner diameter D and the average bubble or slug length in a train of multiple bubbles formed by segmentation.

As is commonly known, the flow of liquid through the channel 3 follows the law of Hagen-Poiseuille:

$$Q = \frac{\pi D^4 \Delta P}{128 \eta_l L} \quad (1)$$

where Q is the volumetric flow rate, D is the hydraulic diameter of the flow channel, ΔP is the pressure difference between the inlet and the outlet of the flow channel, L is the length of the flow channel and $\eta_l$ is the viscosity of the liquid. Rearranging equation (1) provides:

$$\Delta P = \frac{128 Q \eta_l L}{\pi D^4} \quad (2)$$

as an expression indicating the pressure drop required to drive the flow rate Q of liquid through the channel 3.

In the case of a flow of gas through the channel 3, the same equation (2) would apply with the viscosity $\eta_g$ of the gas substituted for the viscosity $\eta_l$ of the liquid.

In the case of bubble fragmentation, it is known that each gas bubble requires a deformation pressure drop to move along the channel 3. The pressure drop is caused by the fact that the front and rear surface of a bubble take on different shapes during movement of the bubble. The deformation pressure drop, $\Delta P_d$ can be represented as:

$$\Delta P_d = \frac{4\alpha\gamma}{D} \quad (3)$$

where α is a frictional surface parameter, that is established empirically, γ is the surface tension between the liquid and air, and D is the hydraulic diameter of the channel. The value of α is a constant, where 0≤α≤1, with 0 representing a perfectly smooth surface and 1 representing a rough surface. Thus, the pressure drop required to drive a bubble along the channel 3, $\Delta P_b$, is the sum of the viscous and deformation pressure drops:

$$\Delta P_b = \frac{4\alpha\gamma}{D} + \frac{128Q\eta_g L_b}{\pi D^4} \quad (4)$$

where $L_b$ is the length of channel taken up by the bubble. On the other hand, because a gas bubble replaces a plug of liquid of the same length and the viscosity of gas is generally lower than the viscosity of liquid, a gas bubble may flow more easily through the channel 3 than a plug of liquid of the same length. Combining equations (2) and (4) yields:

$$\Delta(\Delta P) = \frac{-128Q\eta_l L_b}{\pi D^4} + \frac{128Q\eta_g L_b}{\pi D^4} + \frac{4\alpha\gamma}{D} \quad (5)$$

The replacement of a plug of liquid with a gas bubble leads to no change in the pressure drop through the flow channel 3 (i.e., $\Delta(\Delta P)=0$), if:

$$0 = \frac{-128Q\eta_l L_b}{\pi D^4} + \frac{128Q\eta_g L_b}{\pi D^4} + \frac{4\alpha\gamma}{D} \quad (6)$$

where $L_b$ is again the length of the bubble that replaces a plug of liquid of equal length. In equation (5), if $\Delta(\Delta P)>0$, the insertion of a bubble increases the pressure drop, which leads to a risk of clogging the flow channel 3 with bubbles, whereas if $\Delta(\Delta P)<0$, the insertion of a bubble reduces the pressure drop and poses no risk to the continued flow through the channel.

Rearranging equation (6), a limiting bubble length $L_{bl}$ can be defined as $$L_{bl} = \frac{\pi\alpha\gamma D^3}{32Q(\eta_l - \eta_g)} \quad (7)$$

Bubbles shorter than indicated by equation (7) can lead to a risk of clogging the flow channel, because the gain from lower viscosity of the gas is offset by the loss due to deformation; bubbles longer than indicated by equation (7) may flow freely along the flow channel, because the gain from lower viscosity of the gas dominates.

Whether actual clogging will occur typically depends on the pressure margin that is available for driving the flow. Clogging will usually occur if the total pressure differential between the source 12 and the recipient 13 is consumed by the sum of pressure drops from a train of bubbles and liquid plugs, according to equations (2) and (4).

As mentioned earlier, the occurrence of bubble fragmentation can be unpredictable in flow restrictors of the conventional type shown in FIG. 1. Investigation has shown, however, that the flow restrictor geometry may be modified to suppress the generation of bubbles below a critical length.

Figure 2:
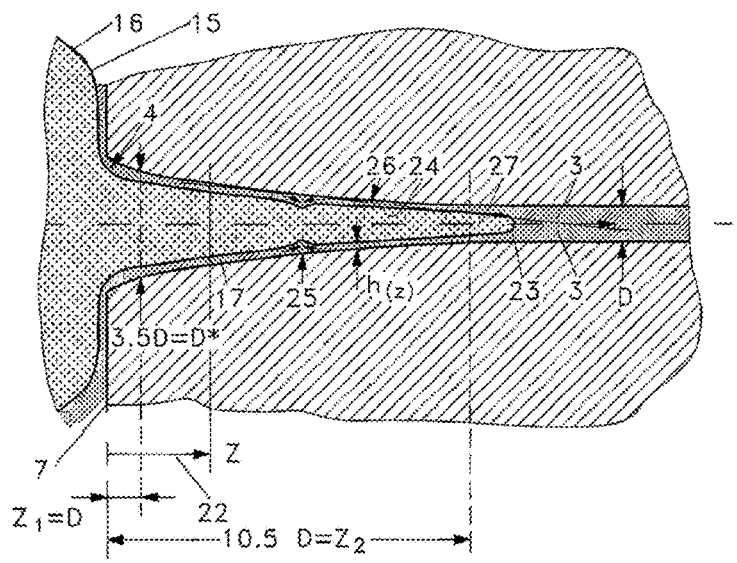
FIG. 2 is a schematic, side cross-section view of a prior art flow restrictor having a converging inlet.

One example of such a modified geometry is shown in FIG. 2. Shown in FIG. 2, on a larger scale than in FIG. 1, is the inlet end of a flow restrictor of a similar overall construction as in FIG. 1. The difference, however, is that the flow channel 3 has been smoothly and gradually widened at the inlet to form a trombone-shaped inlet mouth. Near the inlet face 7, the channel is relatively wide. Further away from the inlet face the channel tapers toward the original internal diameter D. With reference to the coordinate z set at zero at the inlet face 7 and pointing in the direction of flow as indicated at 22, at z=D, in some embodiments, the channel may have an internal diameter $D(z) \geq 3.5$ D, and at $z \geq 10.5$ D the channel may have an internal diameter $D(z) = D$.

In some instances, a first rule for the widening of the channel 3 may be derived from the condition that the inlet geometry should at least allow the formation of bubbles long enough to avoid blocking of the channel 3. Letting N denote the number of bubbles present in the flow restrictor, flow will typically not be blocked if:

$$N\Delta P_d < \Delta P \quad (8)$$

where $\Delta P_d$ is the deformation pressure drop of each bubble as defined in equation (3) above and $\Delta P$ is the pressure drop through the flow channel. We now consider the pinch-off of a bubble in the widest part near the inlet face 7 of the flow channel 3 at a point where the channel has an internal diameter $D^*>D$. $D^*$ represents the diameter of the bubble at pinch off. The volume of a bubble of length $L_{min}=\beta D^*$ at this point can be approximated as:

$$V_b = \beta D^* \frac{\pi}{4} D^{*2} = \frac{\beta\pi}{4} D^{*3} \quad (9)$$

As defined above, β is the aspect ratio of the bubble, a dimensionless constant, that is equal to a ratio between inner diameter D and the average bubble or slug length in a train of multiple bubbles formed by segmentation. β is always theoretically expected to be greater than 1 for fundamental physical reasons, and has not been experimentally observed smaller than 1.5.

The maximum number N of such bubbles in a flow channel of length L is equal to the volume of the channel divided by the volume of a bubble, represented by the following:

$$N = \frac{\frac{\pi}{4}D^2 L}{\frac{\beta\pi}{4}D^{*3}} = \frac{LD^2}{\beta D^{*3}} \quad (10)$$

Entering equation (10) in equation (8) and combining with equations (2) and (3) above, provides:

$$\frac{LD^2}{\beta D^{*3}} \frac{4\alpha\gamma}{D} < \frac{128Q\eta_l L}{\pi D^4} \quad (11)$$

which can be rearranged to give:

$$D^* > \sqrt[3]{\frac{\alpha\gamma\pi D^5}{32\beta\eta_l Q}} \quad (12)$$

The physical interpretation of equation (12) is as follows. If the inlet of the channel 3 is widened to a diameter slightly above $D^*$, this at least creates the possibility that bubbles produced by fragmentation are long enough to not completely stop the flow through the channel, even if the channel is filled up completely by such bubbles.

Turning now to the study of the fragmentation process itself, FIG. 2 shows a bubble 16 of gas 15 entering the channel 3. At the front 23 of the bubble, liquid is displaced by the gas to form a thin film 17 of thickness h(z) on the inner surface of the channel 3. Due to surface tension at the gas-to-liquid interface 24, the film 17 is often unstable. The surface tension exerts a pumping action causing a tendency of the liquid to flow both radially and axially, as shown at 25, which is a well-known phenomenon in the field of hydrodynamics. This causes local accumulation of liquid that may eventually lead to the formation of a plug of liquid which fills the channel 3. Thus a smaller bubble 18 (not shown in FIG. 2) may be pinched off from the larger bubble 16.

It is contemplated to be largely a matter of local surface curvature and timing whether pinch-off will actually occur or not. If the bubble 16 passes a site 25 of beginning local accumulation of liquid, but the liquid film 17 does not reach sufficient thickness to form a liquid plug while the bubble passes, pinch-off will usually not happen. On the other hand, if the liquid film 17 grows thick enough to coalesce at the center of the channel 3 to form a liquid plug while the bubble 16 flows past the site 25, pinch-off usually results.

In some instances, by suitably widening the inlet of the flow channel dependent on the desired flow rate, it is possible to control the timing of perturbation growth of the liquid film around gas bubbles in the channel 3, such that any bubble fragmentation will lead to bubbles that are either longer than the limiting length of equation (7) and thus pose no risk of blocking the capillary or short enough to reduce the flow but not numerous enough to stop the flow of liquid through the capillary.

From experimental and numerical studies, it is known that, for small capillaries, a bubble moving along a straight capillary with the bubble velocity v(z) is surrounded by a liquid film of thickness h(z), represented as:

$$h(z) = \left(\frac{v(z)\eta_l}{\gamma}\right)^{\frac{2}{3}} R(z) \quad (13)$$

where γ is the surface tension at the liquid-gas interface and R(z) is the radius of the bubble at location z. See Bretherton, F. P. 1961 *J. Fluid Mech.* 10:2, 166. In practice, the radius of the bubble may be essentially the same as the radius of the tube, due to the small flow rates and flow velocities considered. The liquid film between the bubble and the tube wall may have a thickness on the order of 1 nm. As one would expect, a slowly moving bubble is surrounded by a thinner film of liquid than a faster-moving bubble. In case of standstill, a bubble will eventually displace all surrounding liquid and dry out the surface of the channel around it.

For small capillaries, any bubble 18 moves at nearly the same velocity as the surrounding liquid. Therefore:

$$v(z) = \frac{Q}{\pi R(z)^2} \quad (14)$$

where v(z) denotes the velocity of a bubble at the location z. For a bubble of length $L_b$ this leads to a bubble transit time $\tau_b$ at the location z of:

$$\tau_b(z) = L_b/v(z) \quad (15)$$

Bubble velocity has a characteristic (maximum) value v* at some coordinate z along the channel 3 where R(z) is at its minimum. Accordingly, bubble transit time has a characteristic (minimum) value $\tau_b$ when:

$$\tau_b = L_b/v^* \quad (16)$$

However, not only bubble velocity determines the film thickness. Since the liquid film adheres to the channel surface, it follows the surface closely. As such, film thickness can be influenced by controlling the shape of the channel surface.

As shown in FIG. 2 at 26, the channel surface at any coordinate z within the widened channel portion slopes inward with a slope, a(z), defined as:

$$a(z) = -\frac{dR(z)}{dz} \quad (17)$$

which has a tangent at z with a corresponding tapering angle:

$$\theta_T(z) = \arctan(a(z)) \quad (18)$$

relative to the longitudinal axis of the channel 3, as shown at 27 in FIG. 2. In a similar fashion as with the bubble velocity and transit time above, the maximum tapering angle in the capillary inlet can be defined as $\theta_T^*$.

Within the tapered channel portion, instabilities will typically cause a liquid film of thickness h(z) to coalesce at the center of the flow channel and thereby to pinch off a bubble within a local time period $\tau_p(z)$, defined as:

$$\tau_p(z) = \frac{0.01}{(\theta_T^*)^{1.2}} \left(\frac{R(z)}{h(z)}\right)^3 \frac{3\eta_l R(z)}{\gamma} \quad (19)$$

The smallest of these local time periods, referred to as τ*, governs the time scale of bubble segmentation within the widened part of the channel 3. In some cases, as it is desired to prevent bubble fragmentation into bubbles shorter than the limiting bubble length given in equation (7), and the characteristic (minimum) transit time $\tau_{bl}$ of such bubbles is:

$$\tau_{bl} = L_{bl}/v^* \quad (20)$$

a channel slope designed such that:

$$\tau^* > \tau_{bl} \quad (21)$$

will prevent the formation of bubbles having a length $L_b < L_{bl}$.

Equations (12) and (21) may then be combined in the design of the widened inlet to the channel 3 to form a flow restrictor that is tolerant to bubble fragmentation. For example, in a first section of the channel 3, between the inlet face 7 and a first z-coordinate $z_1$, the channel diameter D may be kept larger than the value D* given by relation (12) above. In this example, the coordinate $z_1$ is defined as the first location along the channel where the channel diameter narrows down to D*. In some instances, this will ensure that any bubble segmentation within the first section does not generate bubbles which are so short as to block the flow completely.

In a second section of the channel, between the z-coordinate $z_1$ and a second z-coordinate $z_2$, the channel may be designed to narrow down gradually towards the original channel diameter D in accordance with the relation (21) above. The second z-coordinate $z_2$ is defined as the first location along the channel where the channel narrows down to its original, overall diameter D. In practical terms this means that the geometry may be designed to minimize the change in surface curvature as the channel narrows down. In some instances, this will ensure that bubbles which have reached $z_1$ unfragmented, or which have been fragmented at $z_1$ into bubbles of non-critical length, will not be further fragmented during their passage along the second channel section, and will enter into the remaining, straight section of channel 3 unfragmented and remain unfragmented there, as well.

While management of bubble fragmentation according to these techniques is beneficial, it has been discovered that passage of bubbles at the outlet of the flow restrictor can and does create problems in instrumented as well as non-instrumented systems. Accordingly, outlet bubble management is critical to a high performance, reliable microfluidic system.

The above description has focused on a flow restrictor having a trombone-shaped inlet mouth; however, significant advantages can be realized with a dual-tapered flow restrictor having a converging tapered inlet and a diverging tapered outlet. When using a dual tapered capillary for accurate flow control together with a constant pressure source, one obtains a more steady flow with reduced flow fluctuation caused by bubbles passing or pinning to capillary end-faces.

Air bubbles pinning to a micro-capillary or other microfluidic flow restrictor inlet or outlet tend to cause a pressure drop through the flow restrictor, as well as deleterious noise in downstream sensor measurements. In accordance with some embodiments of the invention, these effects may be mitigated through the use of a dual tapered micro-capillary flow restrictor, i.e., a flow restrictor with a converging tapered inlet, a tube with a substantially constant internal diameter, and a diverging tapered outlet. In some cases, the converging tapered inlet and the diverging tapered outlet are each symmetric about a central longitudinal axis of the microfluidic flow restrictor. In some cases the converging tapered inlet and the diverging tapered outlet are also symmetric with each other.

Figure 3:
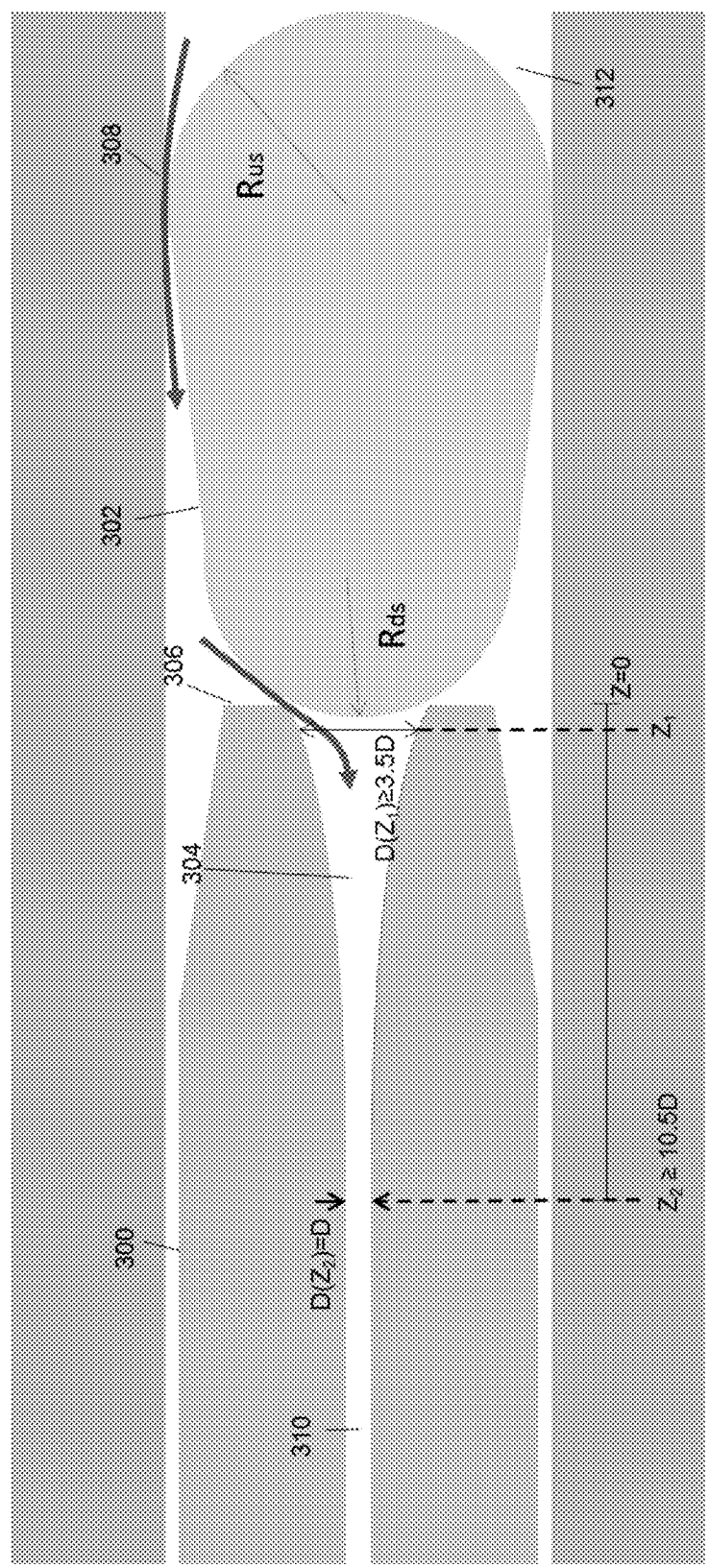
FIG. 3 is a schematic illustration of a bubble at the inlet of a tapered capillary.

FIG. 3 illustrates an example of a microfluidic flow restrictor 300 with a bubble 302 having an upstream bubble radius, $R_{us}$, which is different and larger than a downstream bubble radius, $R_{ds}$, located in front of a tapered flow restrictor inlet 304. The coordinate z may be set at 0 at the inlet face 306 and increase in the direction of flow 308. In some embodiments, the shape of the inlet taper is as follows: at z=D the channel has an internal diameter D(z)≥3.5 D and at z≥10.5 D the channel has an internal diameter D(z)=D. See FIGS. 3-5. Other converging tapers are contemplated. For example, the inlet 304 may narrow down from at least twice the internal diameter (i.e., D(z)≥2D) at the inlet face 306 to the internal diameter D at a constant internal diameter section 310 of the flow restrictor. Alternatively, the inlet 304 may narrow down from at least 1.3 the internal diameter (i.e., D(z)≥1.3 D) at the inlet face 306 to the internal diameter D at a constant internal diameter section 310 of the flow restrictor.

Bubbles can slow or essentially stop flow through microfluidic flow restrictors by creating a pressure drop between upstream and downstream portions of the air bubble. In some examples, a bubble may stop flow altogether if the bubble has been sitting long enough to completely dry a portion of the channel. However, a slow moving bubble allows a thin sheet of liquid to pass around the perimeter, which prevents drying within the channel. The change in pressure ΔP caused by a bubble located at the flow restrictor inlet may be predicted with LaPlace's Law:

$$\Delta P = 2\gamma \left( \frac{1}{R_{ds}} - \frac{1}{R_{us}} \right) \quad (22)$$

where $R_{ds}$ is the downstream radius of the bubble, $R_{us}$ is the upstream radius of the bubble, and γ is the surface tension of the liquid-gas interface formed by the bubble.

The shape of the inlet to the flow restrictor influences the shape of a bubble located in front of the flow restrictor, which leads to changes in pressure drops and flow rate. Exemplary pressure drops, and associated effects on basal dosage volumetric flow rates, are as shown in Table 1 below.

TABLE 1

| Example | $R_{ds}$ [μm] | ΔP [mbar] | Basal rate effect [%] |
|---|---|---|---|
| Perfect taper end-face | 200 | 0 | 0% |
| Typical taper end-face | 50 | 16 | −2.0% |
| No taper or severe damage | 6.5 | 155 | −19.3% |

Table 1 provides exemplary data for an embodiment in which the fluid within the microfluidic flow device with a 13 mm diameter capillary is insulin and the width (i.e., diameter) of the channel in the flow restrictor 312 is 400 μm, or $2R_{ds}$. The pressure drop across the entire flow system is 800 mbar. The pressure drop across the air bubble, ΔP, may be found using equation (22). In this example $R_{us}$ is the same as the channel radius, i.e. 200 μm, and γ=0.052 N/m, the surface tension of insulin. When the inlet is perfectly tapered (i.e., there are no surface imperfections), a bubble would have $R_{ds}=R_{us}$ and there would be no pressure drop across the bubble. The bubble would have no effect on the flow rate. However, in reality, a flow restrictor with a typical tapered inlet may more likely result in the formation of a bubble at the inlet with $2*R_{ds}$=100 μm and $2*R_{us}$=400 μm. Here, the change in $R_{ds}$ from the perfect taper scenario is an artifact of the overall shape of the end-face. Again, using equation (22), it may be seen that a bubble located in front of a typical tapered inlet causes a pressure drop of 16 mbar, resulting in a −2.0% decrease in the basal flow rate through the flow restrictor. As known, the basal flow rate is the volumetric flow rate of a basal dosage of a medicament, which is a constant, relatively low rate of medicament, as opposed to relatively larger, interspersed bolus doses. Basal and bolus doses are described in greater detail in U.S. Pat. No. 7,517,335, the disclosure of which is incorporated herein by reference in its entirety.

Table 1 also provides data for scenarios in which there is no taper. If there is no taper or if the tapered inlet is severely damaged, a bubble may have a very small downstream radius $R_{ds}$ of 6.5 μm and may cause a 155 mbar pressure drop and −19.3% change in the basal flow rate.

Figure 4:
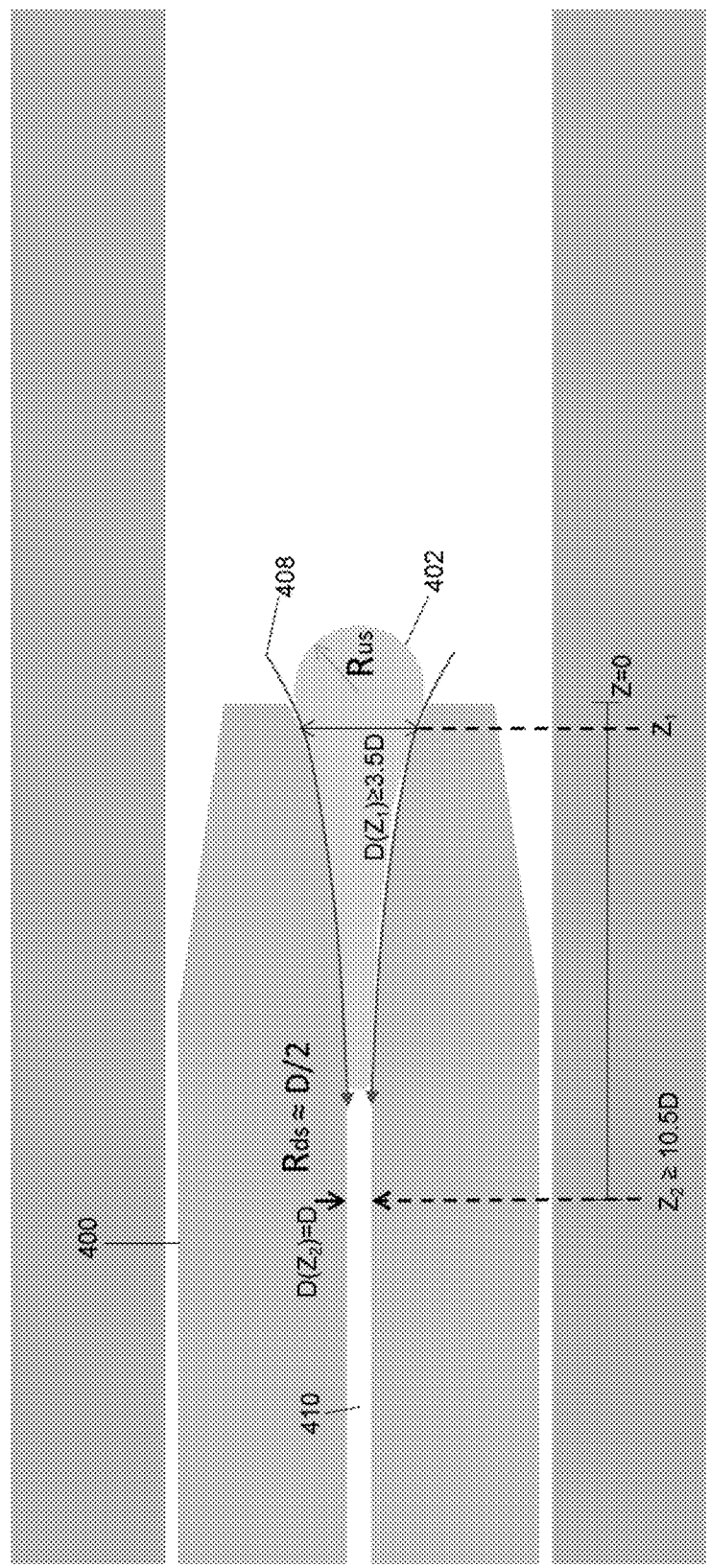
FIG. 4 is a schematic illustration of a bubble at the inlet of a tapered capillary creating a meta-stable condition.

An example may be seen in FIG. 4 of a meta-stable scenario, in which a bubble 402 is temporarily at rest in the inlet 404 of a microfluidic flow restrictor 400. This situation can arise when the pressure drop between the upstream and downstream portions of the bubble is high enough to push the bubble into the inlet, i.e., $$\Delta P > \frac{2\gamma}{R_{us}} \quad (23)$$

but not high enough to push bubble through the flow restrictor, i.e., $$\Delta P < 2\gamma \left( \frac{1}{R_{ds}} - \frac{1}{R_{us}} \right) \quad (24)$$

In the meta-stable scenario, a thin sheet of fluid 408 may flow around the bubble that is resting in the inlet taper when the drive pressure, i.e., ΔP, is too small to move the bubble.

Considering an example in which the bubble moves an infinitesimally small distance $d_z$, it is possible to calculate how far the downstream end of the bubble must move:

$$dz * \frac{A_{us}}{A_{ds}} = dz * \left(\frac{R_{us}}{R_{ds}}\right)^2 \quad (25)$$

where $A_{us}$ and $A_{ds}$ represent the upstream and downstream surface areas of the bubble, respectively.

Similarly, it is possible to calculate the increase in surface area of the bubble when the bubble is pushed a distance dz into the taper. The change in volume upstream equals the change in volume downstream. Therefore:

$$(dz * \pi * R_{us}^2) = \left(dz * \left(\frac{R_{us}}{R_{ds}}\right)^2 * \pi * R_{ds}^2\right) \quad (26)$$

Although the change in the upstream and downstream volumes is equal, the change in wetted perimeter is not equal. The upstream wetted perimeter is $dz*\pi*R_{us}^2$, while the downstream wetted perimeter is $$dz * \left(\frac{R_{us}}{R_{ds}}\right)^2 * \pi * R_{ds}^2.$$

Work performed by a hydraulic system is defined as pressure times displacement. In this example, the work done to move the upstream end of the bubble a distance dz is equal to the increase in surface tension needed to deform the bubble. Equating the work and surface energy and plugging in the above equations yields:

$$\Delta P * \pi * R_{us}^2 * dz = \gamma * \left(dz * \left(\frac{R_{us}}{R_{ds}}\right)^2 * 2\pi * R_{ds} - dz * 2\pi * R_{us}\right) \quad (27)$$

Simplifying equation (27) gives the equation:

$$\Delta P = 2\gamma \left(\frac{1}{R_{ds}} - \frac{1}{R_{us}}\right) \quad (28)$$

In the meta-stable scenario, $R_{us}$ may be estimated to be about half the inlet opening size and $R_{ds}$ may be estimated to be between D/2 and $R_{us}$, where D is the internal diameter of the substantially constant internal diameter section 410 of the flow restrictor.

In the meta-stable scenario, the presence of the air bubble in the microfluidic flow restrictor inlet may cause a pressure drop across the bubble, decreasing flow through the microcapillary. The pressure at the upstream end of the bubble builds until it reaches a critical pressure, $P_{critical}$, that is enough to push the bubble through the flow restrictor. The critical pressure may be represented as $$P_{critical} = \Delta P \quad (29)$$

The exemplary data in Table 2 demonstrates the relationship between the constant internal diameter section size and the critical pressure required to move the bubble. Exemplary $P_{critical}$ for flow restrictors of different internal diameters is as follows:

TABLE 2

| Example | $R_{ds}$ [µm] | $\Delta P = P_{critical}$ [mbar] |
| --- | --- | --- |
| 16 IU/day (min D) | 6.5 | 155 |
| Typical D | 8 | 125 |
| 60 IU/day (max D) | 10 | 99 |

As is seen in the data in Table 2, as the constant internal diameter (D) increases, the pressure differential necessary to move the meta-stable bubble decreases. For the exemplary data shown in Table 2, insulin is the fluid, i.e. γ=0.052 N/m, and $R_{us}$ may be estimated to be greater than 50 µm, i.e., the size of the inlet opening. $R_{ds}$ of the bubble that has been squeezed into the flow restrictor tube is defined as D/2, where D is the internal diameter. In an embodiment in which the flow resistor supplies 16 IU/day, the internal diameter may be 13 µm, which yields $R_{ds}$=6.5 µm. The pressure drop, ΔP, may be calculated using equation (22) yielding the result of ΔP=$P_{critical}$=155 mbar. In another embodiment, the flow restrictor supplies 60 IU/day of insulin and has an internal diameter of 20 µm (i.e., $R_{ds}$=10 µm). Keeping all other variables constant, the critical pressure to move a bubble is 99 mbar. In a flow restrictor having an average internal diameter of about 16 µm (i.e., $R_{ds}$=8 µm), the critical pressure is found to be 125 mbar.

In some instances, upstream system pressure never reaches $P_{critical}$ and the bubble remains pinned to the inlet. In some cases, pressure reaches $P_{critical}$ early in a dosage cycle, such that some bubbles are pushed through, but later in the dosage cycle (e.g., when upstream system pressure decreases as a pressurized bladder decreases in size and associated hoop stress decreases) pressure fails to reach $P_{critical}$, such that later bubbles remain pinned to the inlet. In instances in which pressure fails to reach $P_{critical}$ and the bubble remains pinned to the inlet, a very small flow of fluid can be generated (i.e., fluid sheet 408 that flows around the bubble), in some cases for an extended period of time. Such a low flow rate for such an extended period has been difficult to achieve and can be advantageous in some situations.

Figure 5:
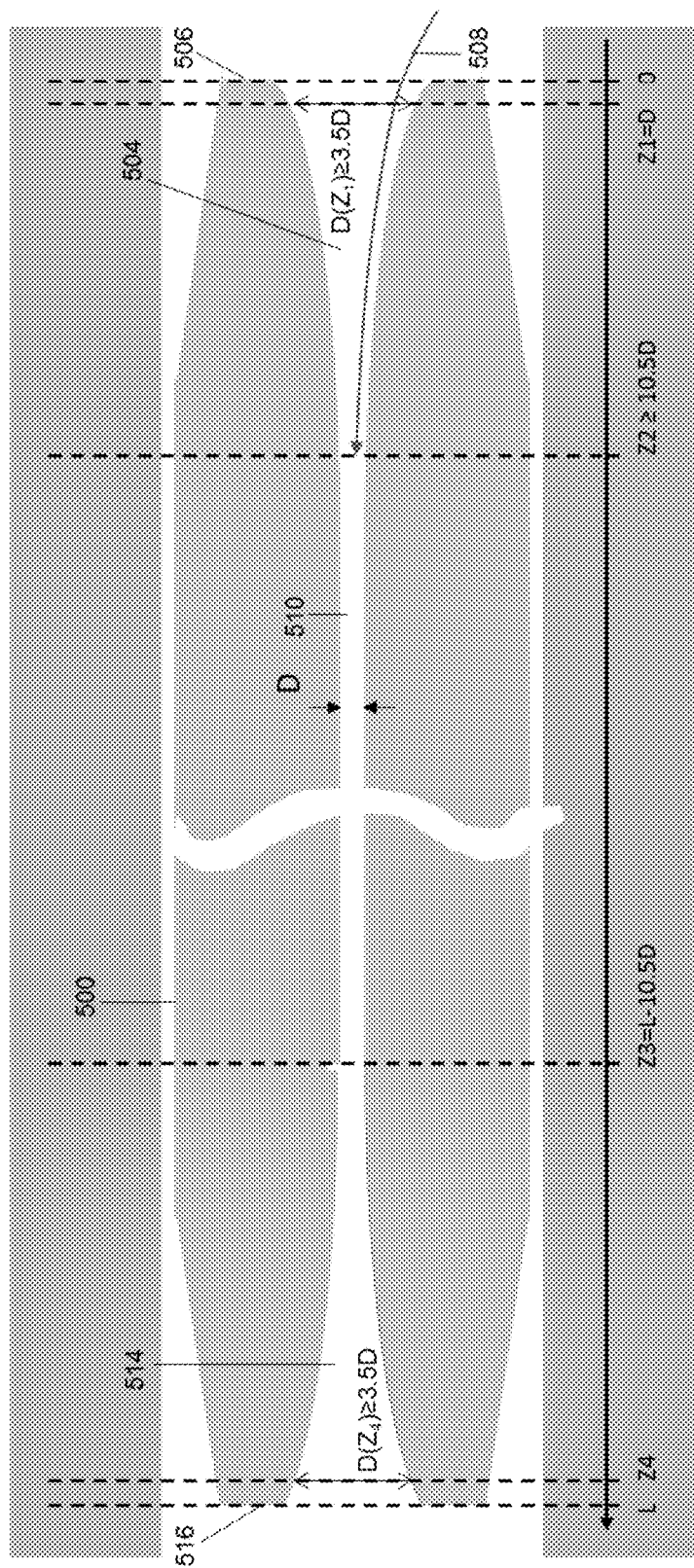
FIG. 5 is a schematic illustration of a micro-capillary with a tapered inlet and a tapered outlet, according to various embodiments.

It has been discovered that even when bubbles push through a tapered inlet and through a constant internal diameter section, bubbles may end up pinned to the outlet of the micro-capillary flow restrictor. Such bubbles pinned to the outlet can generate undesirable noise in flow measurements (e.g., flow pressure measurements). Generation of such undesirable noise can be measurably reduced or substantially eliminated by the use of a diverging tapered outlet, optionally in combination with a converging tapered inlet. Referring to FIG. 5, in an embodiment, a microfluidic flow restrictor 500 has a converging tapered inlet 504 and a diverging tapered outlet 514. The flow restrictor may have a constant internal diameter section 510 therebetween. In some embodiments, in general, a ratio of the length of the microfluidic flow restrictor, L, divided by the internal diameter of the constant internal diameter section 510 (i.e., L/D) may be less than 20,000. In alternative embodiments, the ratio may be less than 500, 1,000, or 10,000. In some embodiments, the ratio may be at least 100, or at least 50, or at least 30, or at least 10. As detailed above, to decrease bubble pinning, the converging tapered inlet may transition gradually and smoothly from the inlet face 506 to the internal diameter section 510. Similarly, the internal diameter section 510 may transition gradually and smoothly to the outlet face 516 to reduce bubble pinning thereat. Proximate the outlet face 516, the flow channel may widen further. The internal diameter at the outlet face 516 may be at least twice as large as the internal diameter D at the constant internal diameter section 510. In one embodiment, the internal diameter D of the constant internal diameter section 510 may be in a range up to about 100 μm, optionally in a range from about 5 μm to about 40 μm. In additional alternative embodiments, the internal diameter of the constant internal diameter section 510 may be in a range up to about 40 μm, 60 μm, or 80 μm. In one exemplary embodiment, the constant internal diameter section 510 begins at a distance of at least twenty times the internal diameter D of the constant internal diameter section downstream of the inlet face 506 and ends at a distance of at least ten times the internal diameter D of the constant internal diameter section upstream of the outlet face 516. As shown in FIG. 5, the coordinate z may be set at zero at the inlet face 506 and may increase toward the outlet face 516. At z=0 the channel may have an internal diameter D(z)≥3.5 D, and at z≥10.5 D the channel may have an internal diameter D(z)=D. Between $z_3$ and $z_4$, the channel may be designed to gradually diverge and open from the constant internal channel diameter D in accordance with the relation (21) above. Accordingly, the outlet geometry can be defined to minimize the change in surface curvature as the outlet opens and, optionally, may be symmetrical with the inlet convergence, as depicted in FIG. 5.

An outlet with the described curvature and smooth tapered surface can be advantageous in preventing bubble pinning. Thus, in some cases, a microfluidic flow restrictor with a tapered inlet and corresponding tapered outlet has advantages over a flow restrictor with only a tapered inlet. The reduction of risk of bubble pinning provided by a smooth outlet taper leads to a reduction in noise in upstream and downstream measurements (e.g., flow and pressure measurements). In some embodiments, the converging tapered inlet and diverging tapered outlet can be symmetric with one another. The symmetric design may, in some cases, simplify the manufacturing of the device.

Figure 6B:
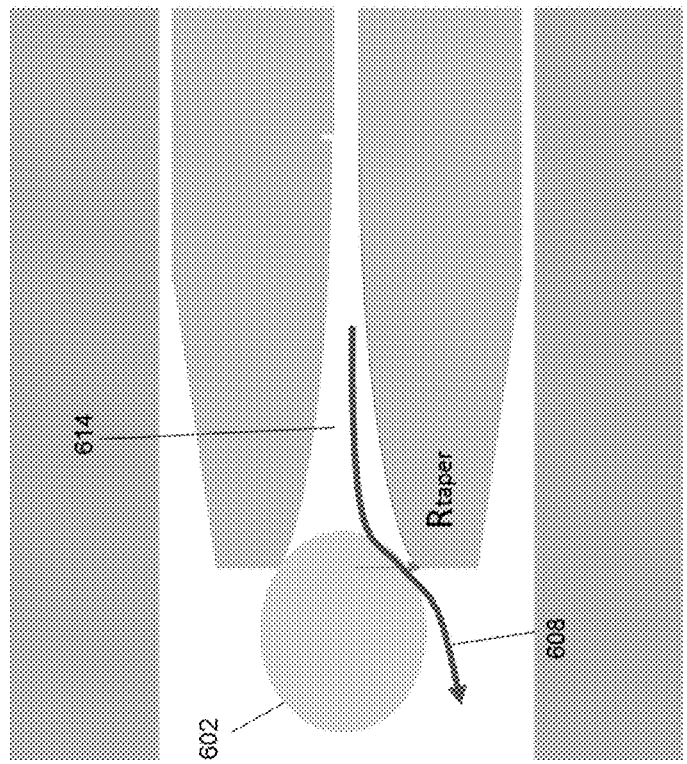
FIGS. 6A-6B are schematic illustrations of a bubble at a tapered outlet and at a non-tapered outlet of a micro-capillary flow restrictor.
Figure 6A:
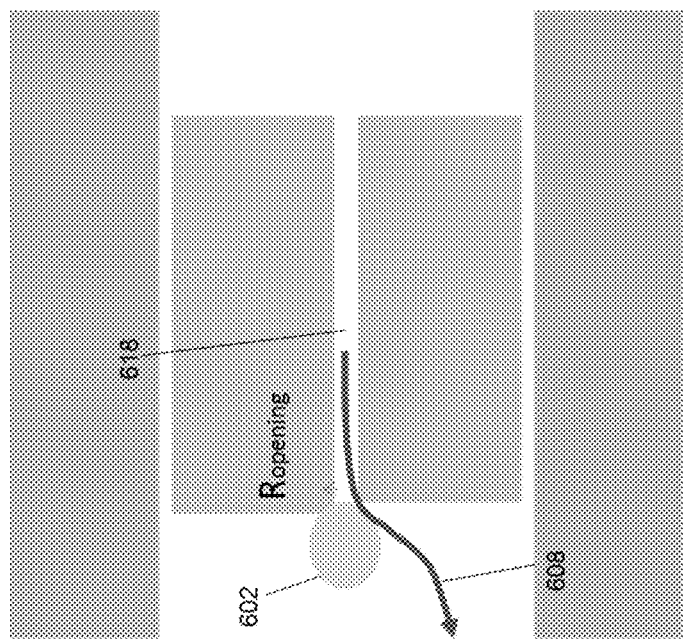

FIGS. 6A-6B illustrate an example of a diverging tapered outlet 614 over a non-tapered outlet 618. FIG. 6A shows a bubble 602 pinned at a non-tapered outlet 618 of a flow restrictor. FIG. 6B shows a bubble 602 at a diverging tapered outlet 614 of a flow restrictor. As bubble 602 exits the outlet portion of a flow restrictor, the bubble generally takes the shape of a sphere, i.e., having a single radius. The pressure drop in this case is governed by the equation:

$$\Delta P = 2\gamma \frac{x}{100}\left(\frac{1}{R_{opening}}\right) \tag{30}$$

where x is the percent of periphery at exit, γ is the surface tension of the liquid-gas interface formed by the bubble, and $R_{opening}$ is the radius of the circular bubble pinned at the outlet opening.

Table 3 displays exemplary data for the effect of the outlet shape of a flow restrictor on the basal flow rate out of the flow restrictor. Exemplary data is given for both tapered and untapered outlets, the untapered outlets having varying amounts of point defects. A point defect is represented by a percentage and indicates a peripheral extent onto which a bubble in the exit flow may become pinned, where 100 percent corresponds to a complete blockage of the outlet. In this exemplary system, the maximum pressure drop that can be maintained is limited by the surface tension γ and the length of perimeter covered by air/liquid interface. The perimeter covered by the liquid air interface may be defined as:

$$L_P = \frac{x}{100} * 2\pi * R_{taper} \tag{31}$$

where $R_{taper}$ is the radius of the tapered opening.

The maximum force experienced in this system may be defined as the length times the surface tension, which is $$F = \frac{x}{100} * 2\pi * R_{taper} * \gamma \tag{32}$$

It is possible to find the maximum pressure drop across the bubble by dividing the force as defined by equation (32), by the hollow core cross sectional area of the taper and simplifying, yielding:

$$\frac{\frac{x}{100} * 2\pi * R_{taper} * \gamma}{\pi * R_{taper}^2} = \gamma * \frac{x}{100} * \frac{2}{R_{taper}} \tag{33}$$

TABLE 3

| Example | $R_{opening}$ [μm] | ΔP [mbar] | Basal rate effect [%] |
|---|---|---|---|
| Perfect end-face, untapered | N/A | 0 | 0% |
| Small point defect, untapered (x = 5%) | 7 | 7 | −0.9% |
| Step at end-face, untapered (x = 70%) | 7 | 100 | −12.5% |
| Step at end-face, tapered (x = 70%) | 38 | 20 | −2.5% |

The exemplary data in Table 3 provides an additional illustration of the improvement of a capillary having a diverging tapered outlet as compared to a non-tapered capillary in real-life environments. As shown in Table 3, if an outlet has a perfect untapered end face, then ΔP=0 and the basal rate is not affected. Of course, in real-life implementations an untapered outlet will always have some defects onto which a bubble can become pinned. For example, if there is a 5% point defect, the ΔP=7 mbar and the basal rate is reduced by 0.9%. As a more extreme example, if the untapered end face has a 70% point defect, then ΔP=100 mbar and the basal flow rate is reduced by 12.5%. Conversely, use of a diverging tapered outlet results in a significantly lower detrimental effect on basal flow rates. For example, in a tapered outlet with the same 70% point defect, the ΔP=20 mbar and the basal flow rate is only reduced by 2.5% (i.e., an 80% improvement).

Figure 7:
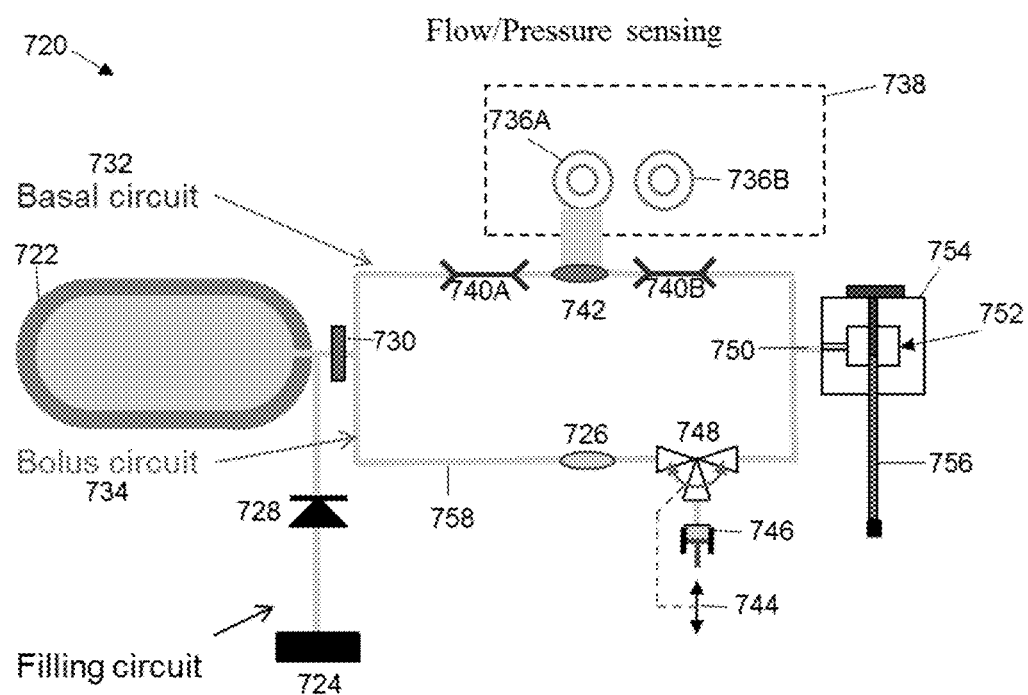
FIG. 7 is a schematic diagram of a microfluidic system suitable for use with two twin tapered flow restrictors connected in series, according to various embodiments.

The microfluidic flow restrictor as described above may be used in a device such as a medicament delivery device such as a patch pump for delivering a medicament such as insulin to a patient. In one embodiment, a microfluidic flow restrictor may transport a liquid having a flow rate in the range from about 1 μl/h to about 500 μl/h. FIG. 7 is a schematic diagram of an exemplary infusion device microfluidic circuit 720 that may be incorporated into a fluid medicament delivery device. The microfluidic circuit demonstrates how dual tapered micro-capillary flow restrictors according to the teachings herein may be connected in series in a microfluidic circuit to reduce noise in measurements. Another exemplary infusion device is described in U.S. Pat. No. 8,672,873, the disclosure of which is hereby incorporated by reference herein in its entirety. The exemplary microfluidic circuit 720 includes a pressurized reservoir 722 that is, in this case, an elastomer bladder. Alternatively, any suitable pressure source may be utilized. A fill port 724 is used to introduce fluid, such as insulin, to the microfluidic circuit 720. In this exemplary microfluidic circuit 720, introducing insulin via the fill port 724 fills both the reservoir 722 and a variable-volume bolus reservoir 726. Inlet check valve 728 prevents backflow of insulin and other check valves may be placed in suitable locations in the circuit 720.

During use, insulin is forced from the reservoir 722 by elastic contraction of the elastomer, through a filter 730, and into two parallel flowpaths, a basal flowpath 732 and a bolus flowpath 734. The basal flowpath 732 delivers a constant dose or steady-state level of insulin to a patient; the bolus flowpath 734 delivers a bolus dose of insulin to the patient as needed or desired by the patient, for example, in conjunction with a meal. The basal flowpath 732 includes a first pressure sensor 736A or other pressure or flow sensor in communication with the flowpath 732, for example, at a mid-point in the basal flowpath. In an alternative embodiment, the first pressure sensor 736A or first sensing element may be placed further upstream or downstream in the basal flowpath, as desired. In another alternative embodiment, a plurality of pressure sensors in communication with the basal flowpath 732 may be utilized. A second pressure sensor 736B or second sensing element is exposed to ambient air pressure P. The function of and relationship between the pressure sensors 736A, 736B is described in more detail below. In one embodiment, the pressure sensors 736A, 736B are micro-electronic-mechanical system (MEMS) sensors. Each MEMS sensor is about 2 mm square, but sensors having different dimensions may also be used. Both MEMS sensors are contained within an indicator unit 738 housing system electronics. The pressure sensor 736A communicates with a portion of the basal circuit 732 between two flow restrictors 740A, 740B (e.g., the dual-tapered micro-capillaries, described above). In one embodiment, this portion between the flow restrictors 740A, 740B may be a pressure sensor chamber 742. The first flow restrictor 740A segments any gas bubble entrained in the liquid to a size that may pass through the constant internal diameter section of the flow restrictor. The pressure sensor 736A senses pressure changes in the basal flowpath 732, which may be indicative of upstream or downstream occlusion conditions, such as those caused by an air bubble, that result in a decrease or increase in pressure therein. The pressure sensor 736B senses changes in ambient air pressure external to the fluid medicament delivery device. The pressure sensors 736A, 736B are absolute pressure sensors, but a single relative pressure sensor may also be used. A relative pressure sensor, e.g., a gauge MEMS sensor, may be used to replace both absolute pressure sensors.

To deliver a bolus dose via the bolus flowpath 734, the patient presses a button 744 on the bolus displacement chamber 746 that drives a single stroke (delivering a single dose) of a medicament stored in the bolus displacement chamber 746 and opens two valves that are part of a three-way valve 748. The valves are in series for redundancy safety purposes. The parallel flowpaths 732, 734 join at a common channel 750 just before an internal chamber or a cannula void 752. The cannula void 752 is formed in a cannula base 754, which allows a point of connection to a cannula 756. The cannula 756 extends below the skin of a patient, thus delivering the insulin subcutaneously. In one embodiment, the actuation of the bolus button 744 may be sensed by the indicator unit 738 with, for example, a magnetic sensor, a Hall effect sensor, or a switch. In an alternative embodiment of the microfluidic circuit, at least one pressure sensor may be placed in the bolus flowpath 734, thereby allowing the indicator unit 738 to also sense the actuation of the bolus button 744. Conduits 758 having diameters larger than those of the flow restrictors 740A, 740B connect the various components.

Figure 8:
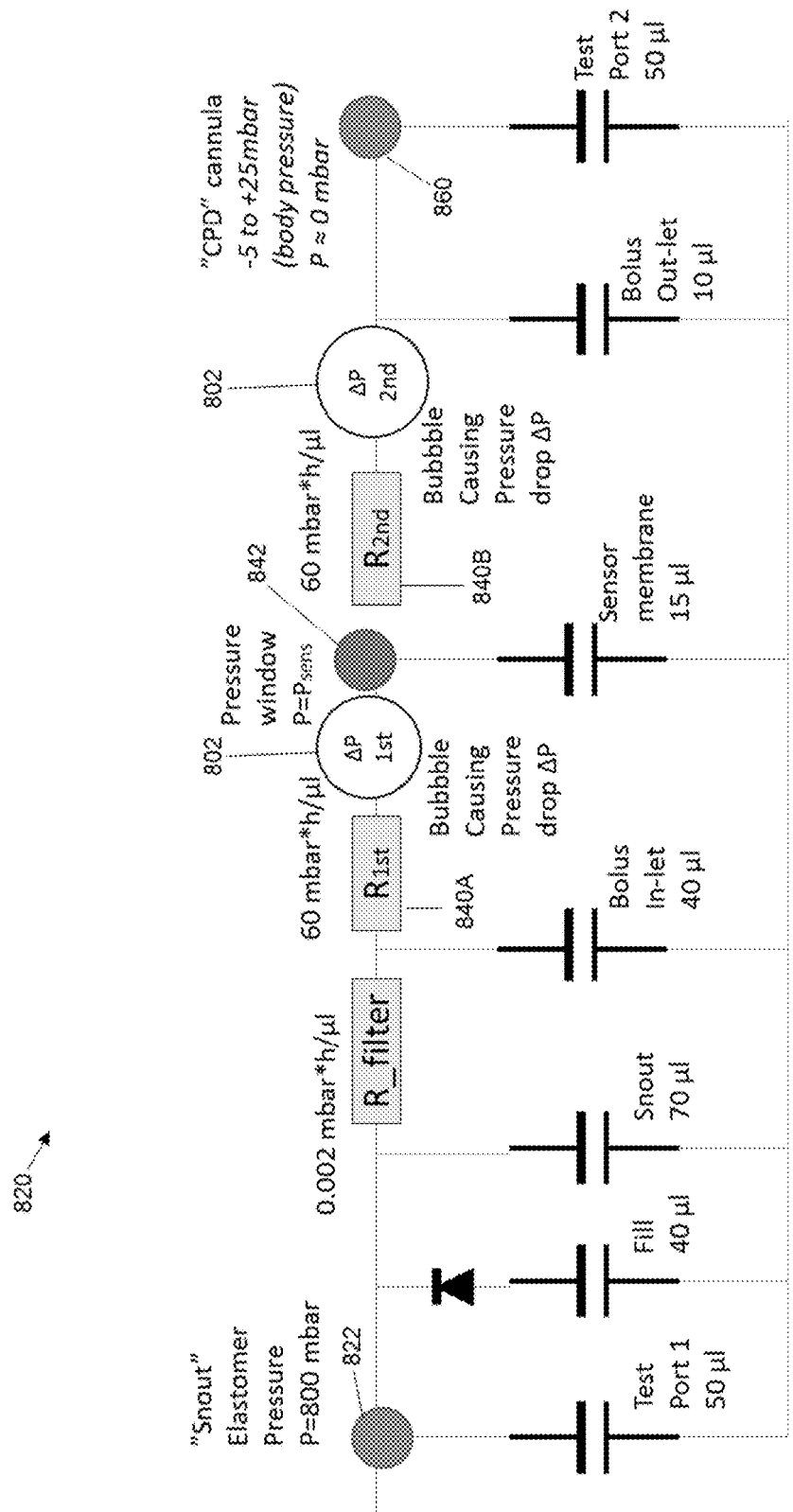
FIG. 8 is a schematic diagram of another microfluidic circuit system using twin tapered flow restrictors connected in series, according to various embodiments.

FIG. 8 illustrates a schematic of an exemplary microfluidic circuit 820 with a drive pressure of 800 mbar demonstrating the pressure drop between the pressurized reservoir 822 and a cannula placement device 860, that inserts the cannula 756 (FIG. 7) into a patient's skin. In this exemplary circuit, a bubble 802 is present at an inlet of each of two flow resistors 840A, 840B arranged in serial flow relationship. Each bubble creates a pressure drop that may affect the measurement of pressure by the pressure sensor in the pressure window 842 between the two flow resistors 840A, 840B.

In this exemplary circuit 820, it is possible to detect whether or not a bubble has pinned to the first or second flow restrictor 840A, 840B. When measured pressure increases while flow decreases, the system is said to be counter phase and signifies a bubble pinning to the second flow restrictor 840B. When flow decreases and measured pressure also decreases the system is said to be in phase and signifies a bubble pinning to the first flow restrictor 840A. However, it may not be possible to distinguish if the bubble is pinning to the upstream or downstream end of the flow restrictors 840A, 840B.

In some instances, the use of dual tapered capillaries in series, as shown for example in FIG. 8, is advantageous since these flow restrictors are adapted to reduce the noise component in pressure and flow measurements by an measureable amount (e.g., 10%, 20%, 30%, 40%, 50%, 60%, 70%, etc.). Additionally, as previously described, the diverging outlet taper reduces bubble pinning and, therefore, reduces the effect of bubbles on the pressure measurements taken at pressure window 842.

As described with reference to FIG. 7, the indicator unit 738 contains two pressure sensors 736A, 736B. The indicator unit 738 may be programmed to conduct a pressure reading periodically, for example, about every 30 minutes, to monitor the status of the fluid medicament delivery device. Periodic pressure readings allow the indicator unit 738 to alert the patient to, and differentiate between, a change in fluid pressure caused by occlusions/partial occlusions and a change in fluid pressure caused by the final contraction phase of the elastomer reservoir 722, just prior to overall system pressure dropping to zero. The electronic components contained within the indicator unit 738 may determine that a change in pressure during the early operational life of the device is due to an occlusion (e.g., a blocked cannula 756). Further, the indicator unit 738 may determine that a change in pressure during the late stages of operation of the device is due to the final contraction phase of the elastomer reservoir 722. Regardless, upon detection of a pressure change of a predetermined threshold valve, the patient is alerted that the device is not working properly and that the patient attachment unit 759 needs to be replaced.

The fluid medicament delivery device may operate properly in various external pressure environments, for example, while a patient is at sea-level, at elevated pressure conditions (i.e., below sea-level), and at decreased pressure conditions (i.e., above sea-level). Additionally the components contained within the indicator unit 738 are able to distinguish pressure changes caused by occlusions from those caused by changes in ambient pressure, due to ambient pressure sensor 736B. The fluid medicament delivery device will continue operating normally in various external pressure environments and, thus, alert the patient to changes in pressure that are only due to conditions that require attention to the device (e.g., an occlusion, a partial occlusion, or a near-empty condition of the elastomer bladder 722). Thus, there are important benefits to the patient in receiving accurate pressure readings and status through the indicator unit 738. The use of dual tapered capillaries connected in series reduces the risk of inaccurate pressure measurements due to noise or deleterious pressure fluctuations due to flow path occlusion caused by air bubbles.

EXPERIMENTAL EXAMPLES

Figure 9:
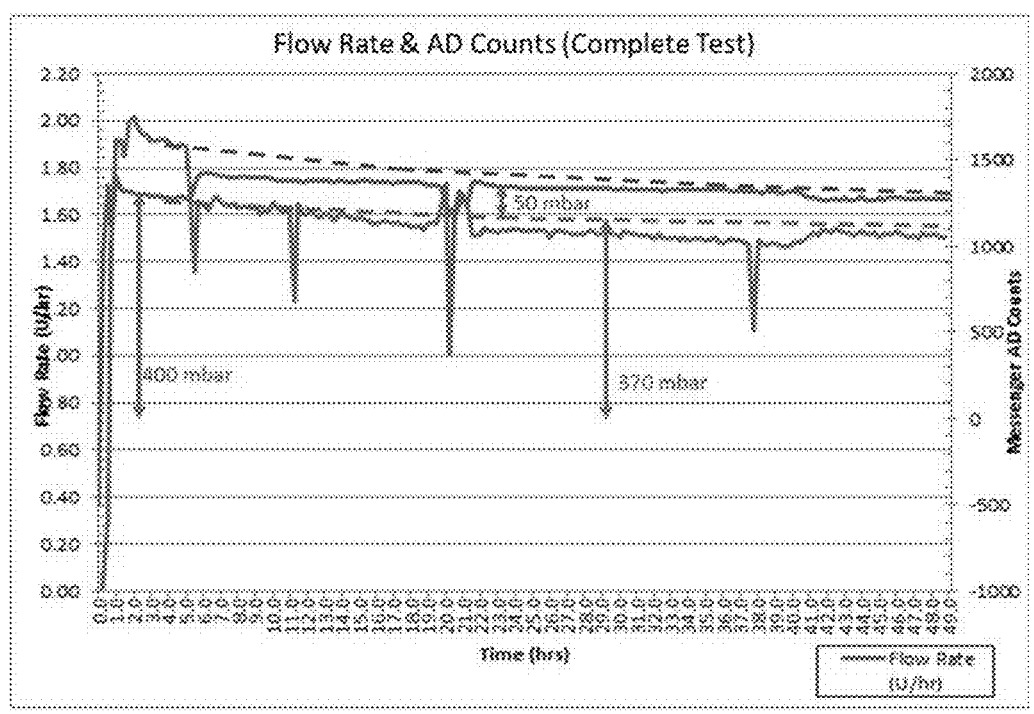
FIGS. 9-14 are a series of graphs displaying experimental data demonstrating improvements using embodiments of the invention.

FIG. 9 shows graphical flow rate and pressure data taken from pressure and flow rate sensors in an infusion patch pump. The data collected is from a system containing two flow restrictors with a tapered inlet and a non-tapered outlet connected in series around (i.e., upstream and downstream of) a flowpath sensor membrane. The fluid in the system is insulin.

FIG. 9 contains a graphical display of 49 hours of pressure and flow rate data. As seen in FIG. 9, Messenger AD Count corresponds to the output of the MEMS pressure sensor, which is converted from an mV signal to a digital number representing measured pressure by a microcontroller analog-to-digital converter (ADC). In this example, the pressure sensitivity of the MEMS pressure sensor has been experimentally determined to be about 3.25 ADC/mbar.

In FIG. 9, the dotted line is an approximation of a hypothetical flow through the device without any bubbles. This approximation was established based on the known profile of the elastomeric bladder pressure profile. The graph in FIG. 9 shows a temporary 50 mbar pressure step caused by a bubble creating a 100 mbar pressure drop across itself. A pressure of about 400 mbar is detected, as the MEMS pressure sensor only detects half of the actual bubble effect. If pressure across the bubble is 100 mbar, then the pressure drop across the two flow restrictors is 350 mbar each, and therefore the pressure in the sensor window will either increase to 450 mbar, if the bubble is located at the downstream flow restrictor or decrease to 350 mbar, if the bubble is located at the upstream flow restrictor. The spikes or blips in the data are flow measurement artifacts.

FIGS. 10-13 show graphical flow rate and pressure data take from sensors in an infusion patch pump, such as that depicted in FIG. 7. The data collected is from a system containing two dual tapered capillary flow restrictors with a tapered inlet and a tapered outlet connected in series around a sensor membrane. The fluid in the system is insulin. This experimental data demonstrates the benefits of the inclusion of an outlet taper in a flow restrictor.

Figure 10:
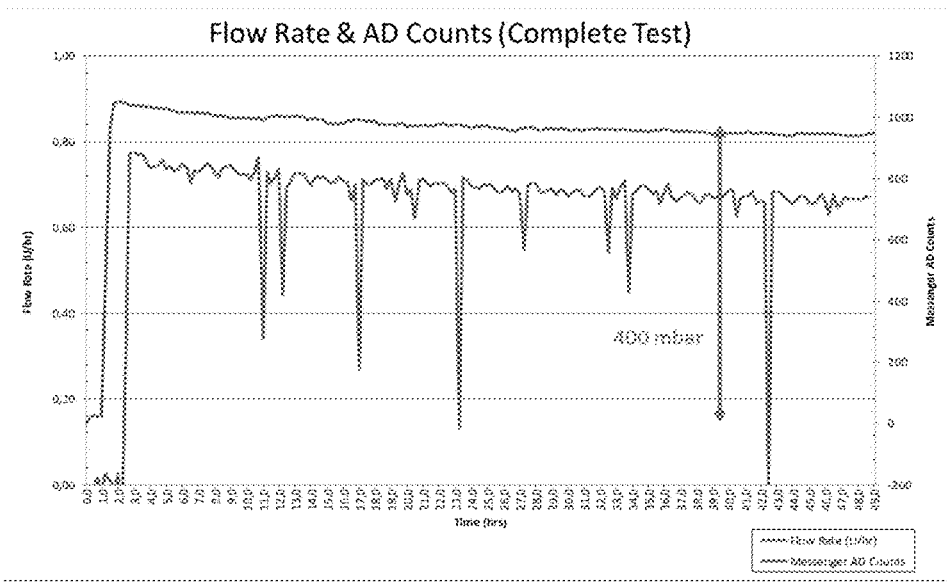

FIG. 10 is a graph depicting flow rate and messenger AD count data taken from a microfluidic system with twin tapered capillary flow restrictors connected in series around a sensor membrane. The fluid in the system is insulin. When taken in comparison with FIG. 9, the noise in the pressure data is reduced and is only about 4 mbar. The system flow is about 20 IU/day.

The downward spikes seen in FIG. 10 may be attributed to a test artifact related to dissolved air in the liquid. When liquid goes from a pressurized state to ambient pressure conditions, it will out-gas a small amount of air that accumulates in small air bubbles pinning to various parts of the system. As described above, the inlet and outlet of a flow restrictor constitute such places for accumulation of air bubbles, but bubbles may also accumulate at the outlet of the cannula extending into a test vial placed on a scale during measurement. In general, there may be a small air bubble at the end of the cannula, which tends to grow slowly as it is fed by out-gassing of the liquid flowing past the bubble. As this bubble grows to a critical size of about 1.5-2 μl, it will detach from the tip of the cannula and rise to surface of liquid in the collection vial. The effect on the measured output mass in the system is an abrupt decrease of weight by about 1.5-2 mg corresponding to the buoyancy effect caused by the pinned bubble's sudden detachment. Since the flow is calculated based on a mass versus time measurement, an abrupt downward step in mass translates to a negative spike in the calculated flow rate.

Figure 11:
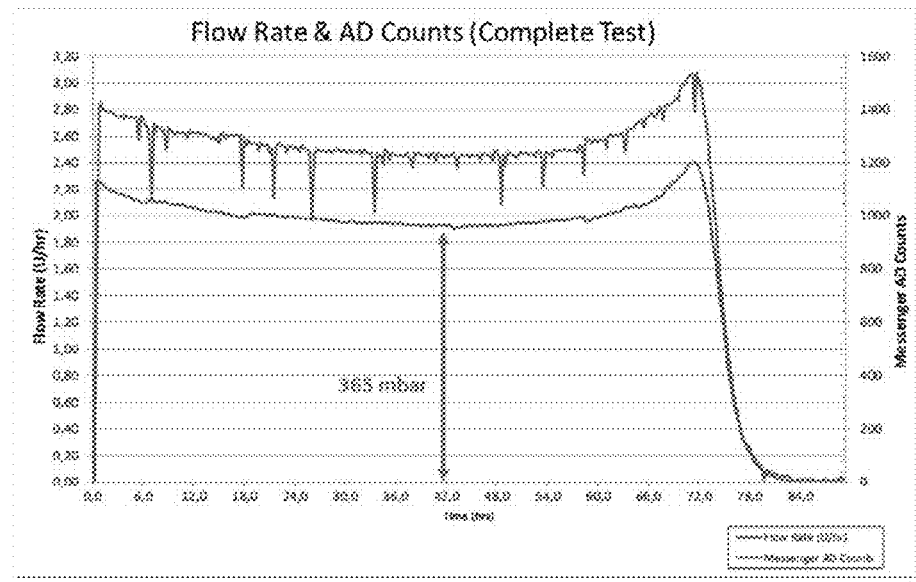

FIG. 11 is a graphical representation of experimental flow rate and pressure data for an infusion pump device with a flow rate of 60 IU/day of insulin. This data shows smooth curvature, indicating that no bubbles were present throughout the period of measurement. Both the flow rate and pressure go to zero as the device reservoir empties of insulin.

Figure 12:
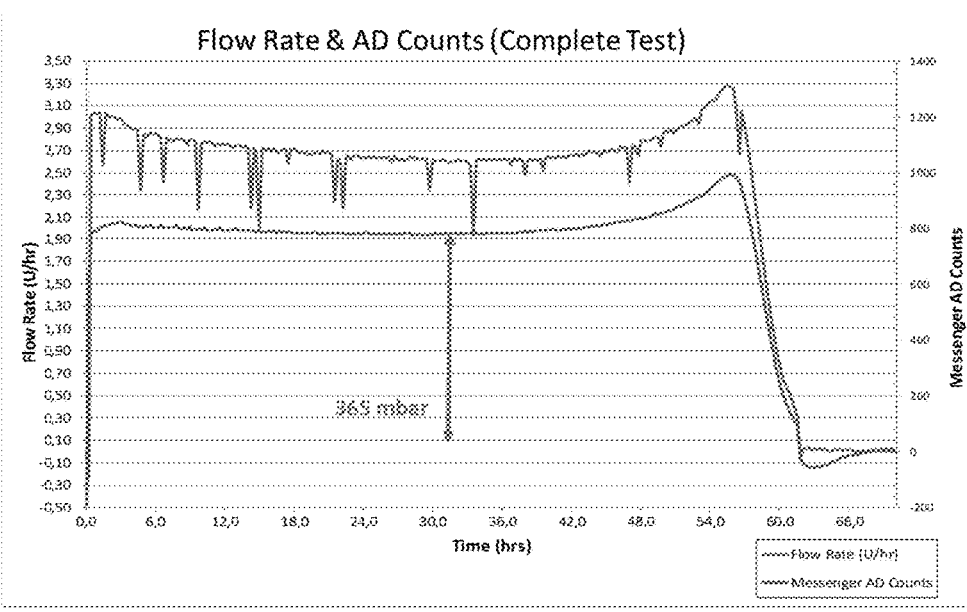

The effect of a bubble in a similar 60 IU/day system may be seen in the data of FIG. 12 at about time=62 hr. At time=62 hr, the pressure drops to zero and the flow rate drops to about 0.1-0.2 μl/h. This data is consistent with the model of a bubble at the inlet of the first or upstream flow restrictor connected in series. The observed noise in the pressure data is about 5 mbar.

Figure 13:
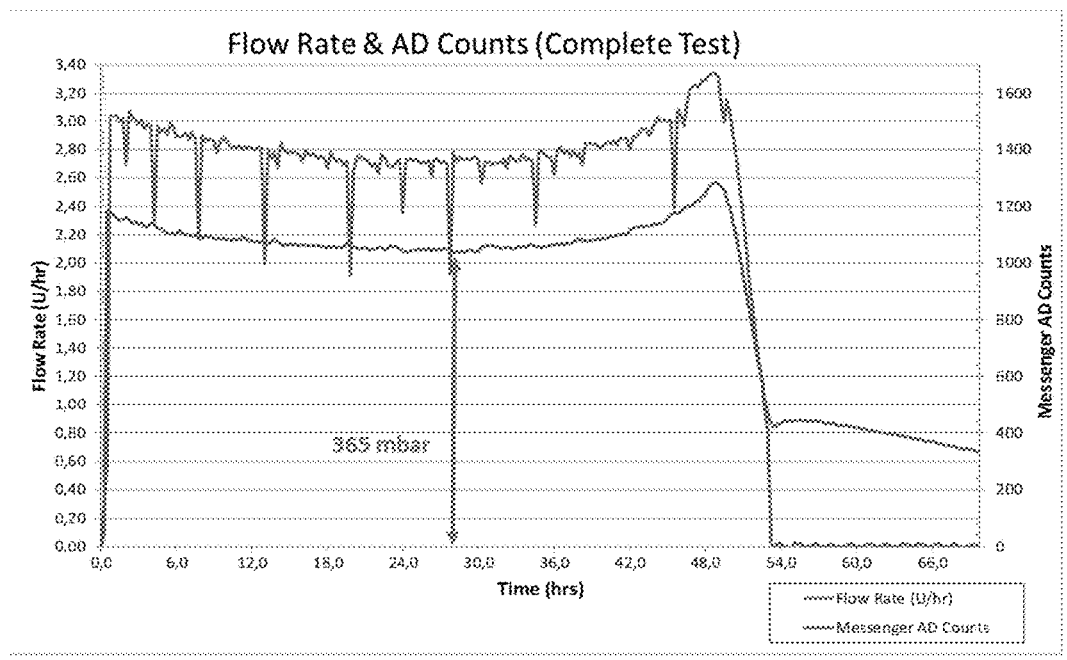

A bubble at the inlet of the second or downstream flow restrictor connected in series is shown in the data displayed in FIG. 13 in a similar 60 IU/day system. In this example, pressure remains constant at about 140 mbar with a very slow decay. In the period from 54 h to 68 h, pressure decreases from 140 mbar to 120 mbar, while the flow is very small about 0.01 IU/h or 0.1 μl/h. This is close to the predicted value as previously described with respect to Table 2, which predicts a pressure of 125 mbar for this typical flow restrictor diameter. The observed noise in the data is about 7 mbar.

Figure 14:
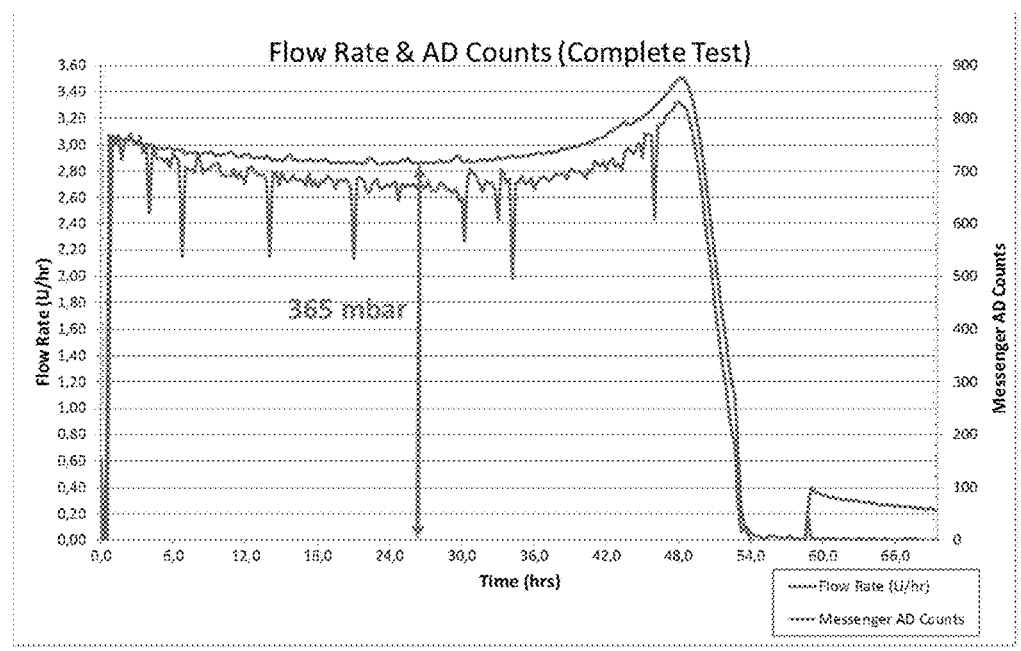

Two bubble events are observed in the data displayed in FIG. 14. The bubble enters the first flow restrictor inlet at time=53 hr, marked by a pressure and flow rate drop to zero. After about six hours, the pressure gradually steps up to about 100 ADC, which corresponds to about 50 mbar and gradually decreases. Simultaneously, the flow rate picks up to about 0.1-0.2 μl/h, which, as previously discussed, is consistent with a bubble at the inlet of the second flow restrictor.

During experimentation several factors were shown to influence the basal flow rate. Table 4 displays a non-exhaustive list of exemplary factors and their minimum and maximum effect on the nominal flow rate in an infusion patch pump device having a pair of flow restrictors in series, each with a tapered inlet and a non-tapered outlet.

TABLE 4

| Factor | Flow Decrease | Flow Increase |
|---|---|---|
| Capillary flow resistance | −4.0% | +4.0% |
| Elastomer pressure | −3.0% | +3.0% |
| Confounded (RMS) | −5.0% | +5.0% |
| Bubbles | −9.5% | −1.5% |

TABLE 4-continued

| Factor | Flow Decrease | Flow Increase |
|---|---|---|
| Small leaks | −2.0% | 0.0% |
| Bubble-compensation | +6.5% | +6.5% |
| Total | −10.0% | +10.0% |

Table 5 displays a non-exhaustive list of exemplary factors and their minimum and maximum effect on the nominal flow rate in an infusion patch pump device having a pair of flow restrictors in series, each with a tapered inlet and a tapered outlet.

TABLE 5

| Factor | Flow Decrease | Flow Increase |
|---|---|---|
| Capillary flow resistance | −4.0% | +4.0% |
| Elastomer pressure | −4.0% | +4.0% |
| Confounded (RMS) | −5.6% | +5.6% |
| Bubbles | −2.5% | −0.5% |
| Small leaks | −2.0% | 0.0% |
| Bubble-compensation | +2.5% | +2.5% |
| Total | −7.6% | +7.6% |

As seen in the data from Tables 4 and 5, all other factors between the two systems remain roughly constant. However, with the use of flow resistors with a tapered inlet and a tapered outlet, the variability, or noise, in the basal flow rate caused by bubbles decreases significantly from a range of about −1.5 to −9.5% to a range of about −0.5 to −2.5%. This demonstrates the advantageous decrease in the noise in flow measurements when using twin tapered capillary flow resistors connected in series.

This description contemplates flow restrictors designed in accordance with equation (12), equation (21) or both, or any other relationship disclosed herein or any physical interpretation of any such relation. The embodiments shown in the drawings should be considered in a non-limiting fashion as being exemplary of preferred and alternative ways of practicing the invention. Flow restrictors of a similar nature may be made in planar technology by micromachining or embossing techniques, for example. In any realizations, one can connect several flow restrictors in series or parallel for specific purposes.

While various implementations of the present invention have been described herein, it should be understood that they have been presented by way of example only. Where methods and steps described above indicate certain events occurring in certain order, those of ordinary skill in the art having the benefit of this disclosure would recognize that the ordering of certain steps can be modified and that such modifications are in accordance with the given variations. Although various implementations have been described as having particular features and/or combinations of components, other implementations are possible having any combination, sub-combination, or permutation of any features and/or components from any of the implementations described herein.

The invention claimed is:

1. A method of restricting a flow of a liquid, the method comprising:
passing the liquid through a first microfluidic flow restrictor comprising (i) a converging tapered inlet comprising an inlet face and a smooth and gradual transition from the inlet face to a constant internal diameter section and (ii) a diverging tapered outlet comprising an outlet face and a smooth and gradual transition from the constant internal diameter section to the outlet face;
passing the liquid through a second microfluidic flow restrictor in series with the first microfluidic flow restrictor, the second microfluidic flow restrictor comprising (i) a converging tapered inlet comprising an inlet face and a smooth and gradual transition from the inlet face to a constant internal diameter section and (ii) a diverging tapered outlet comprising an outlet face and a smooth and gradual transition from the constant internal diameter section to the outlet face;
flowing a gas bubble entrained in the liquid to the inlet face of the first or second microfluidic flow restrictor;
directing the gas bubble entrained in the liquid into the first or second microfluidic flow restrictor via the converging tapered inlet; and
segmenting the gas bubble entrained in the liquid using the converging tapered inlet of the first or second microfluidic flow restrictor,
wherein a sensor is disposed in a flow path between the first and second microfluidic flow restrictors, the liquid passing though the flow path in operable communication with the sensor.

2. The method of claim 1, wherein at least one of the inlet face and the outlet face of the first and second microfluidic flow restrictors comprises an internal diameter of at least two times an internal diameter of the constant internal diameter section.

3. The method of claim 1, further comprising reducing likelihood of the gas bubble pinning to the outlet face of the first or second microfluidic flow restrictor using the diverging tapered outlet.

4. The method of claim 1, wherein a ratio of a length of each of the first and second microfluidic flow restrictors divided by an internal diameter of the corresponding constant internal diameter section is less than 20,000.

5. A method of measuring a flow characteristic of a liquid in a flow path, the method comprising:
passing the liquid through a flow restrictor in the flow path, the flow restrictor comprising a converging tapered inlet comprising an inlet face and a diverging tapered outlet comprising an outlet face;
obtaining a measurement of the flow characteristic of the liquid downstream of the diverging tapered outlet and outlet face of the flow restrictor using a sensor, wherein the diverging tapered outlet is adapted to reduce a noise component of the measurement;
flowing a gas bubble entrained in the liquid to the inlet face;
directing the gas bubble entrained in the liquid into the flow restrictor via the converging tapered inlet; and
segmenting the gas bubble entrained in the liquid using the converging tapered inlet.

6. The method of claim 5, wherein the flow characteristic comprises at least one of a flow rate and a pressure.

7. The method of claim 5, wherein the sensor comprises at least one of a flow rate sensor and a pressure sensor.

8. The method of claim 5, further comprising reducing likelihood of the gas bubble pinning to the outlet face using the diverging tapered outlet.

* * * * *